US009234900B2

(12) United States Patent
Lee et al.

(10) Patent No.: US 9,234,900 B2
(45) Date of Patent: Jan. 12, 2016

(54) METHOD FOR DIAGNOSING GLIOMA AND SCREENING FOR THE THERAPEUTICS OF GLIOMA THROUGH IDENTIFYING PROTEIN RELOCATION

(71) Applicant: Ajou University Industry-Academic Cooperation Foundation, Suwon-si, Gyeonggi-do (KR)

(72) Inventors: Ki Young Lee, Suwon-si (KR); Bong Hee Lee, Jeju-si (KR); Kyung Hee Byun, Jeju-si (KR); Sun Ha Paek, Seoul (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 0 days.

(21) Appl. No.: 14/059,283

(22) Filed: Oct. 21, 2013

(65) Prior Publication Data

US 2014/0106376 A1    Apr. 17, 2014

Related U.S. Application Data

(63) Continuation-in-part of application No. PCT/KR2012/003110, filed on Apr. 23, 2012.

(30) Foreign Application Priority Data

Apr. 22, 2011 (KR) ........................ 10-2011-0037728

(51) Int. Cl.
*G01N 33/15* (2006.01)
*G01N 33/68* (2006.01)
*G01N 33/574* (2006.01)

(52) U.S. Cl.
CPC ...... *G01N 33/6893* (2013.01); *G01N 33/57407* (2013.01); *G01N 2500/00* (2013.01)

(58) Field of Classification Search
None
See application file for complete search history.

(56) References Cited

FOREIGN PATENT DOCUMENTS

WO    WO 2010/081158 A2    7/2010

OTHER PUBLICATIONS

Lindahl et al. (2001). Human Glial Cell Line-derived Neurotrophic Factor Receptor α4 is the Receptor for Persephin and Is Predominantly Expressed in Normal and Malignant Thyroid Medullary Cells. *The Journal of Biological Chemistry*, 276(12), 9344-9351.
Björling et al. (2008). A Web-based Tool for in *Silico* Biomarker Discovery Based on Tissue-specific Protein Profiles in Normal and Cancer Tissues. *Molecular & Cellular Proteomics*, 7(5), 825-844.
Sreekanthrethly et al. (2010). Identification of Potential Serum Biomarkers of Glioblastoma: Serum Osteopontin Levels Correlate with Poor Prognosis. *Cancer Epidemiology, Biomarkers & Prevention*, 19(6), 1409-1422.
Johansen (2006) Studies on serum YKL-40 as a biomarker in diseases with inflammation, tissue remodeling, fibroses and cancer. *Danish Medical Bulletin*, 53(2), 172-209.
International Search Report, mailed Nov. 30, 2012 in connection with PCT International Application No. PCT/KR2012/003110, filed Apr. 23, 2012.

*Primary Examiner* — Brad Duffy
*Assistant Examiner* — Nelson B Moseley, II
(74) *Attorney, Agent, or Firm* — John P. White; Cooper & Dunham LLP

(57) ABSTRACT

The present invention relates to a method for diagnosing glioma by comparing the protein location of an individual to be diagnosed with the normal control nerve cells. More particularly, the present invention relates to a method for diagnosing glioma including determining that an individual has glioma when the expression level of GFRα4 in the endoplasmic reticulum is higher than that in the plasma membrane, and a method for screening a therapeutic agent for glioma. In the diagnostic method of the present invention, the protein expression levels in particular subcellular locations are compared, thereby accurately diagnosing glioma, diagnosing progression of glioma, and predicting prognosis after glioma surgery.

2 Claims, 43 Drawing Sheets

(using primary cells)

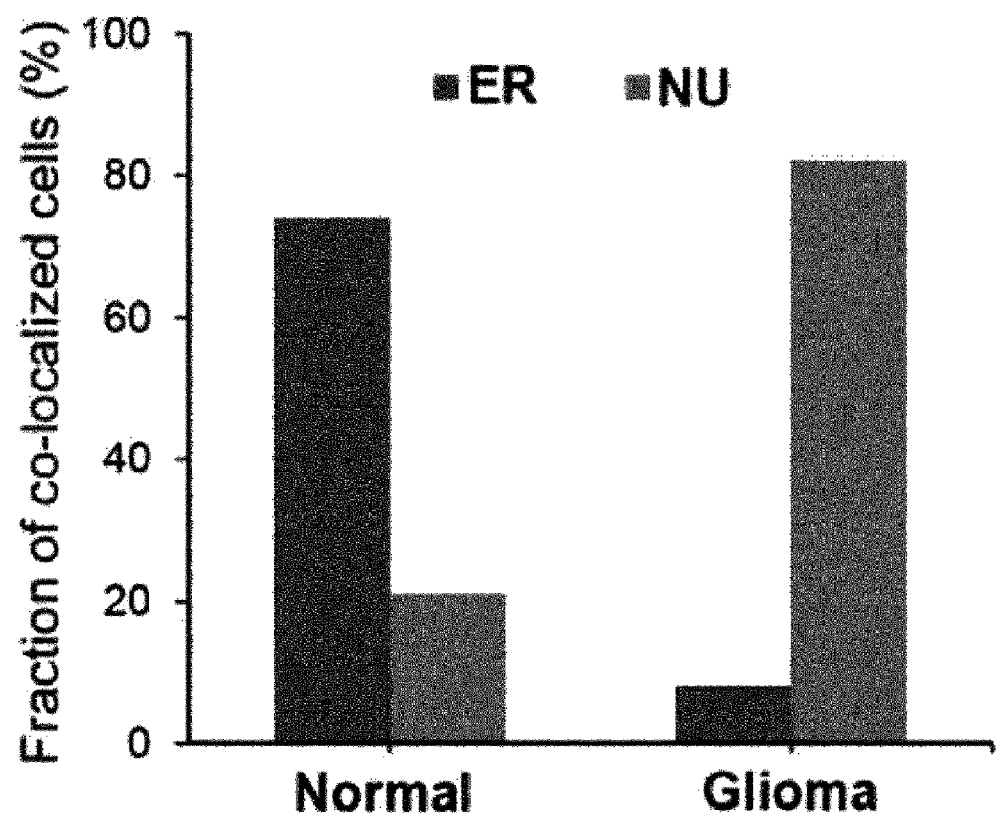
FIG. 9b
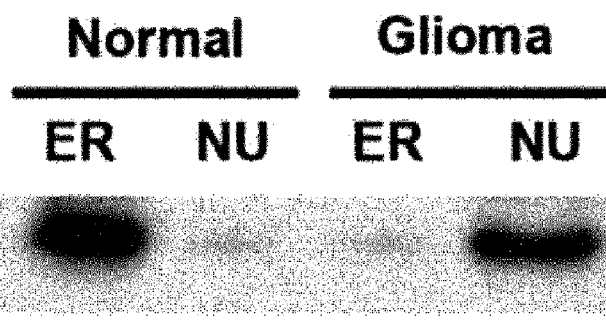

(using tissues)

(using primary cells)

(using tissues)

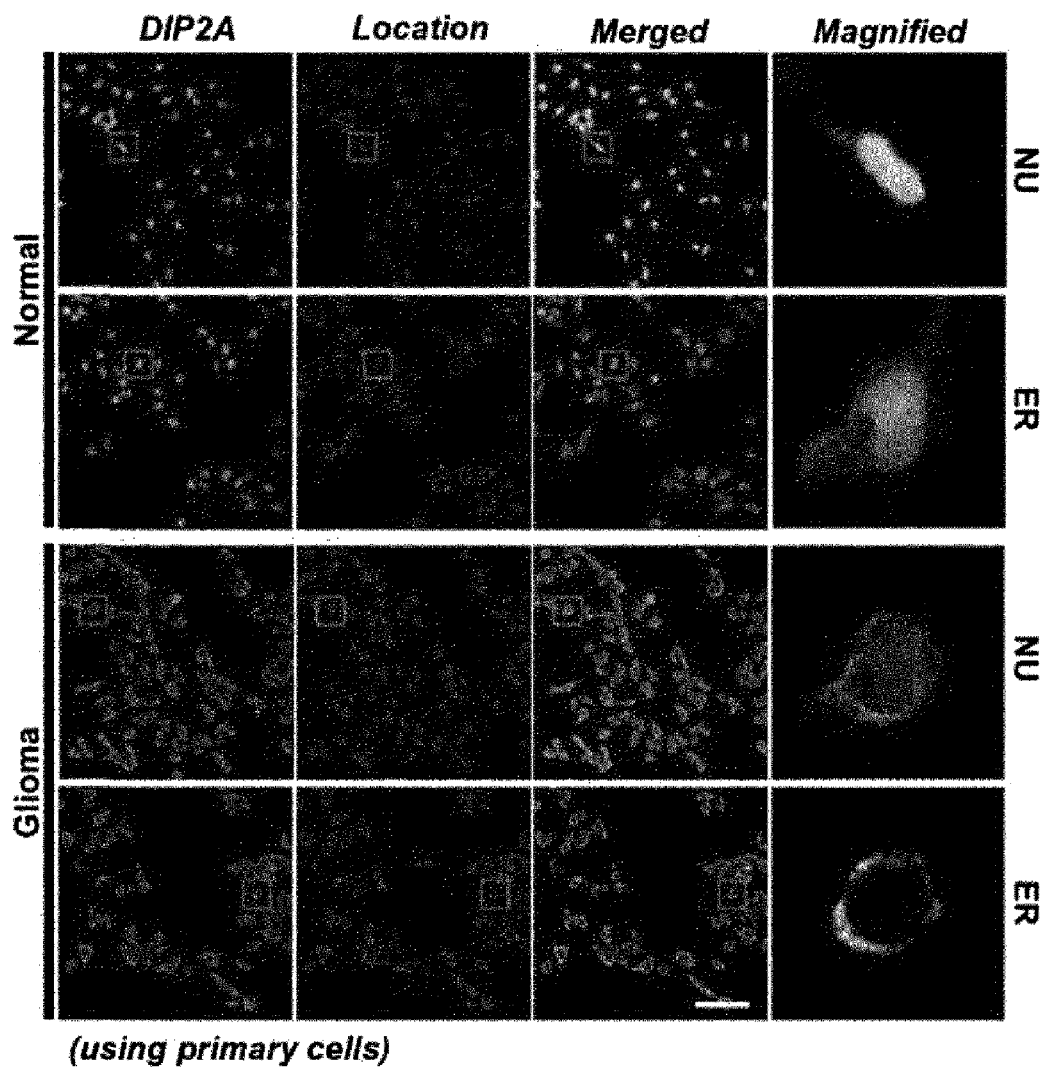

(using primary cells)

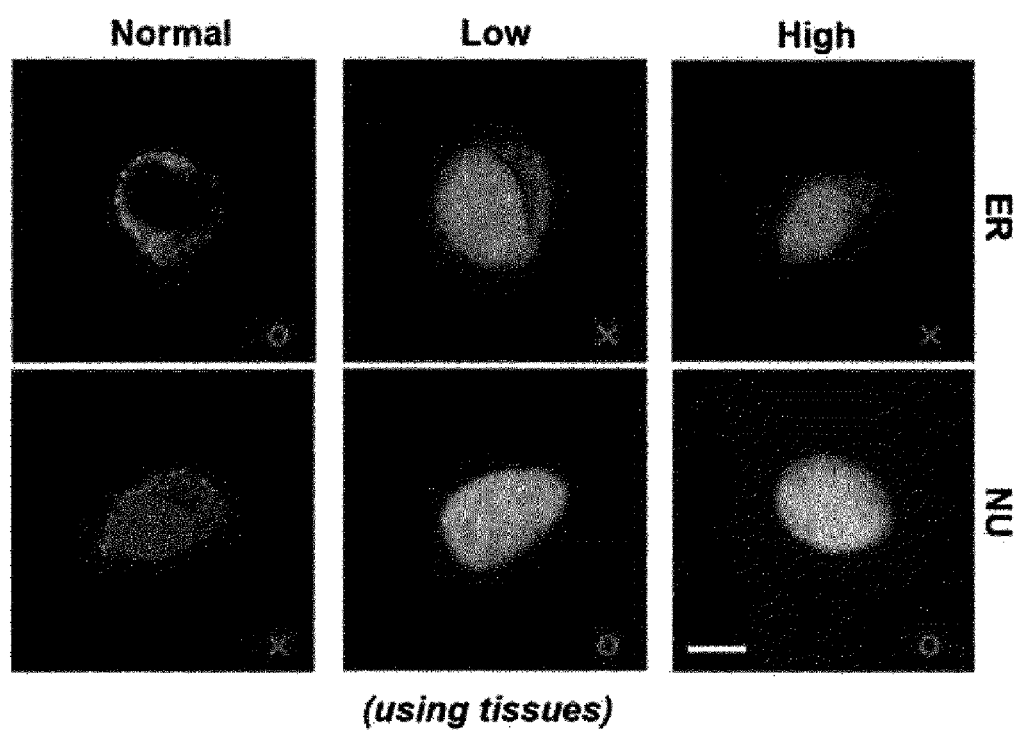

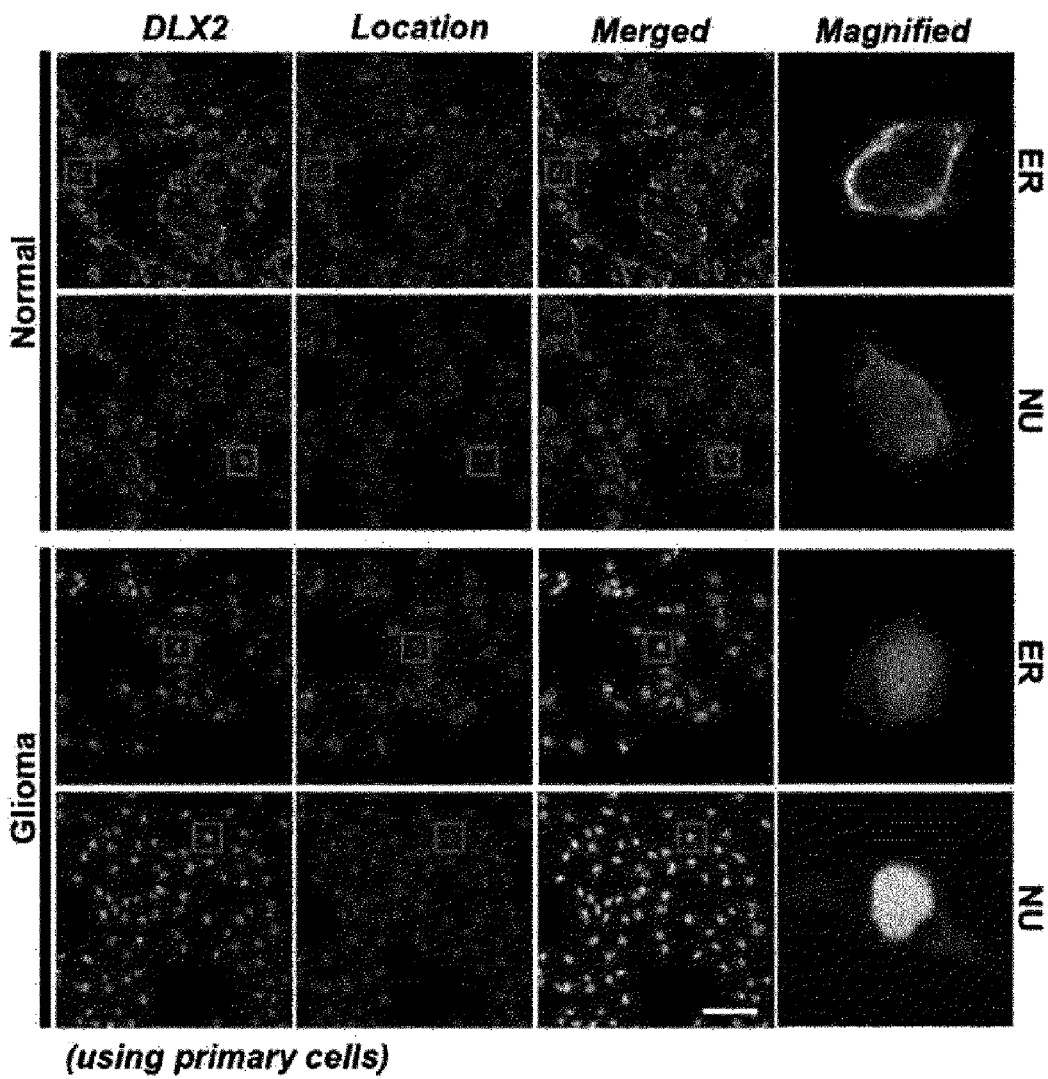

*(using tissues)*

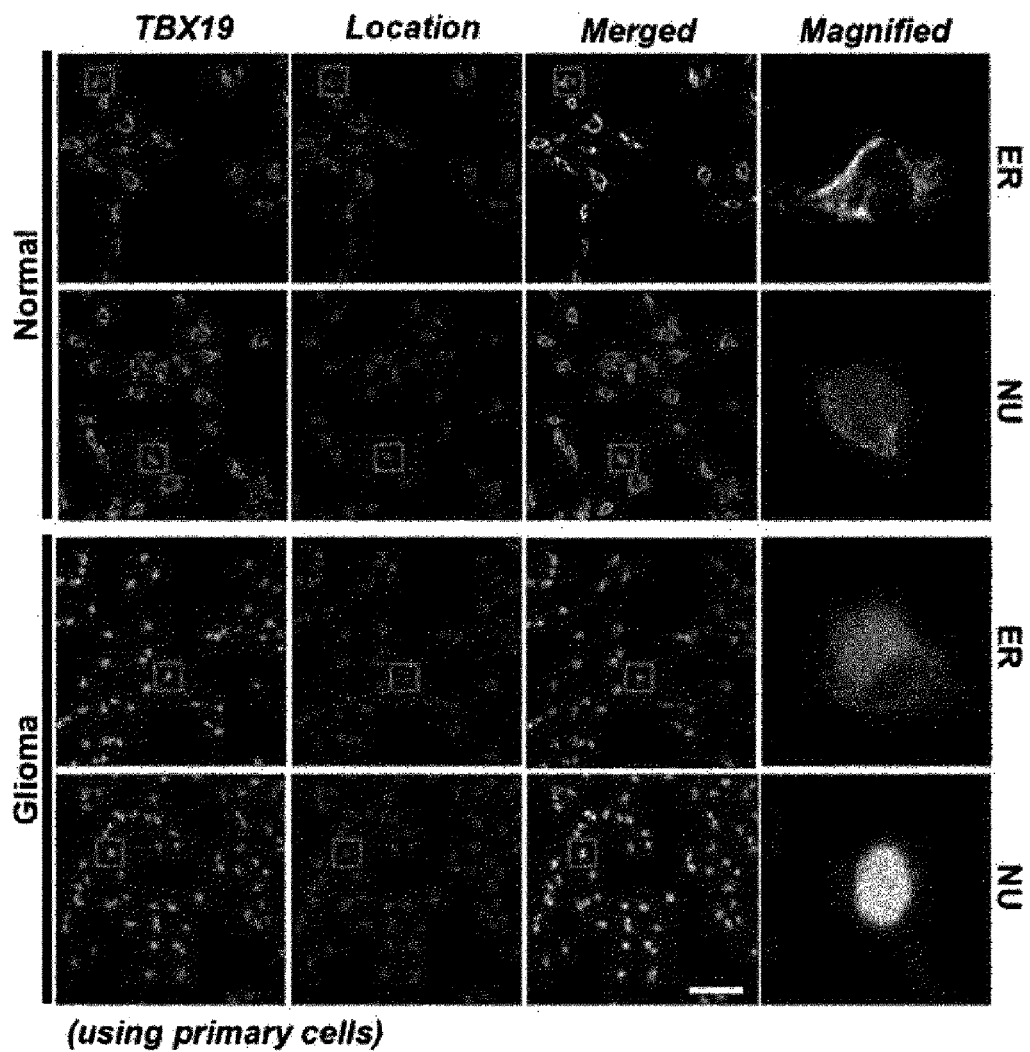

*(using tissues)*

(using primary cells)

(using tissues)

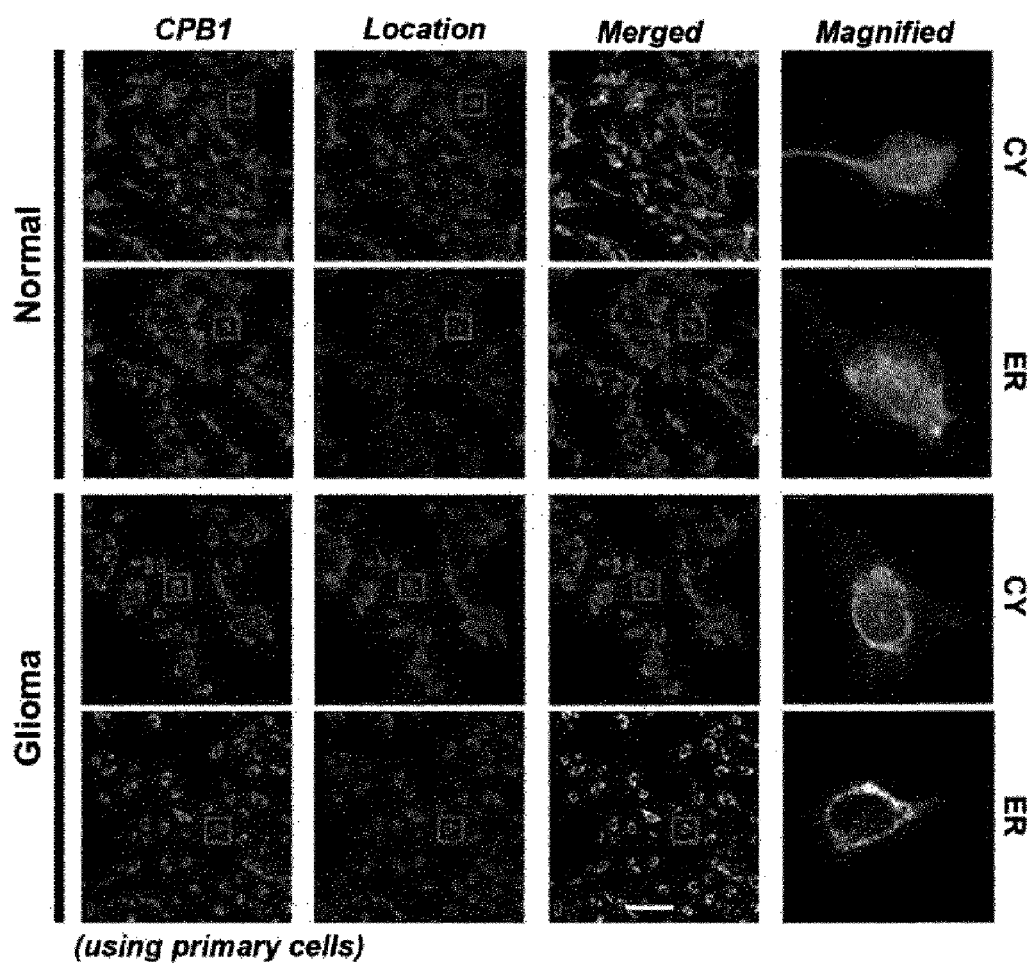
[FIG. 17b]

*(using tissues)*

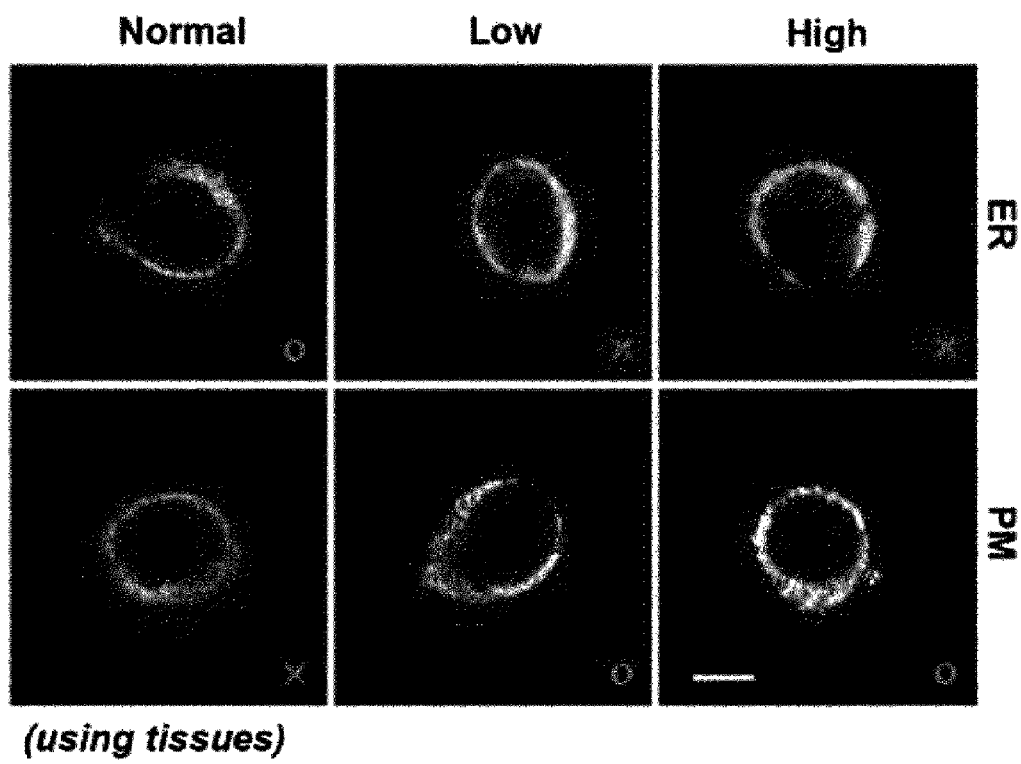

[FIG. 19b]
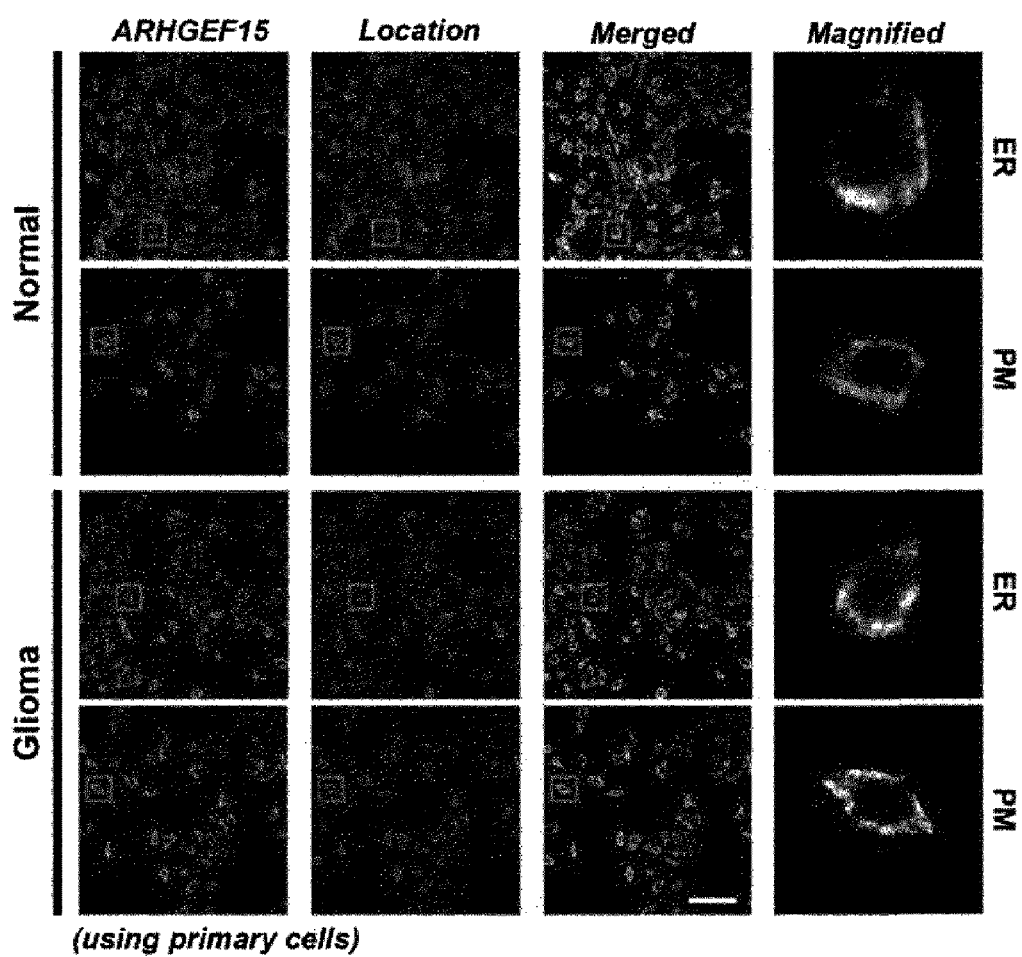
(using primary cells)

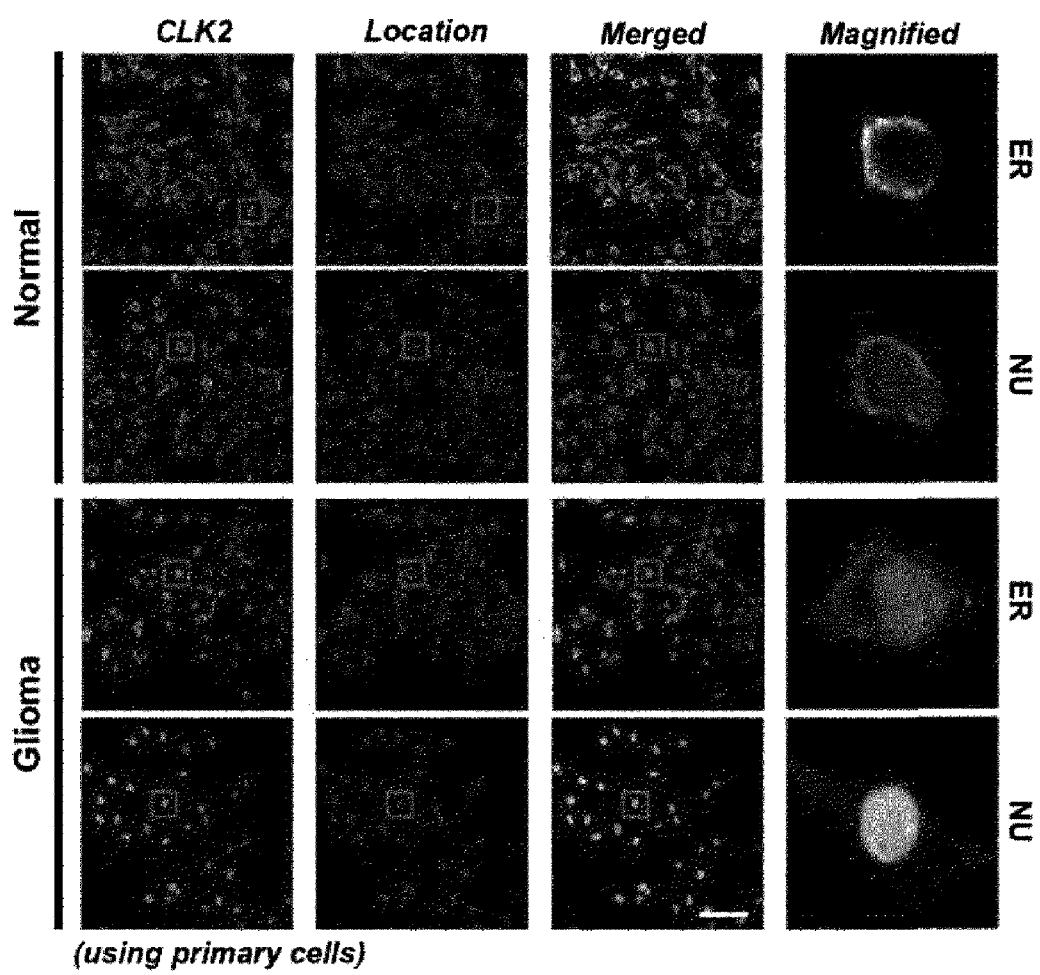

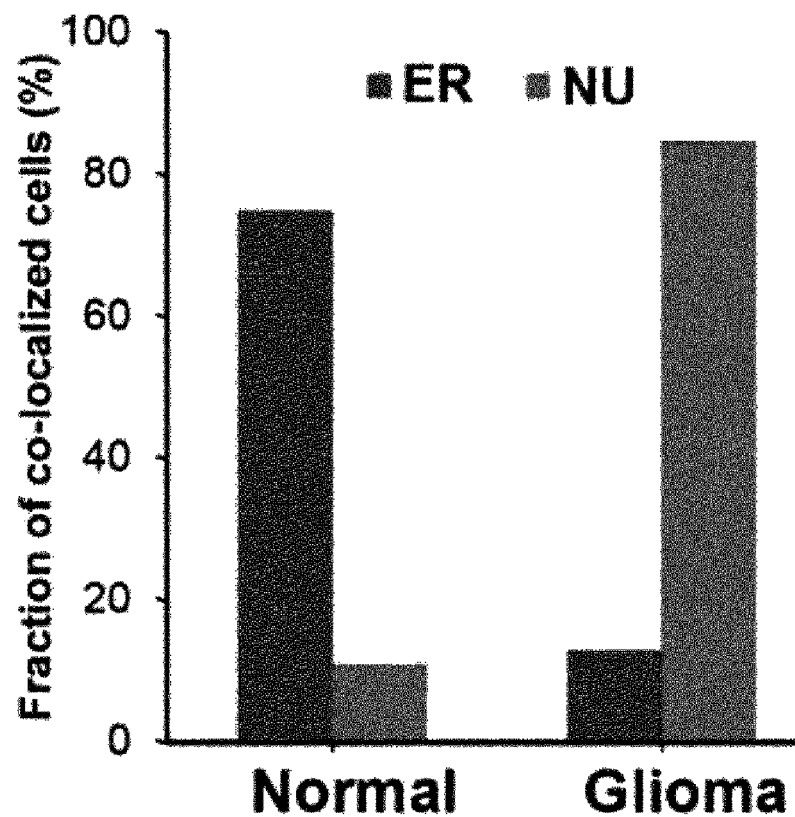
FIG. 20c
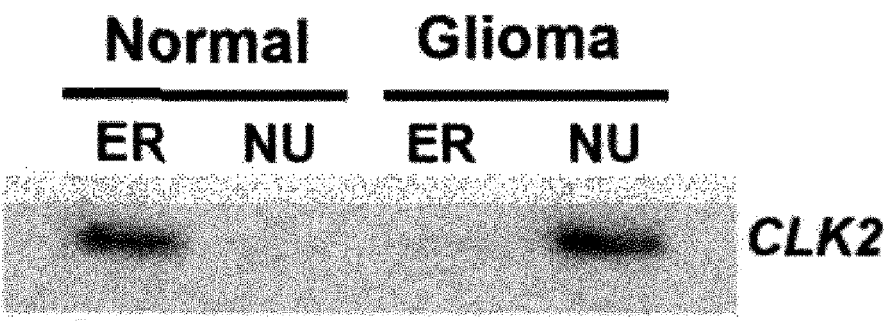

*(using tissues)*

[FIG. 21b]
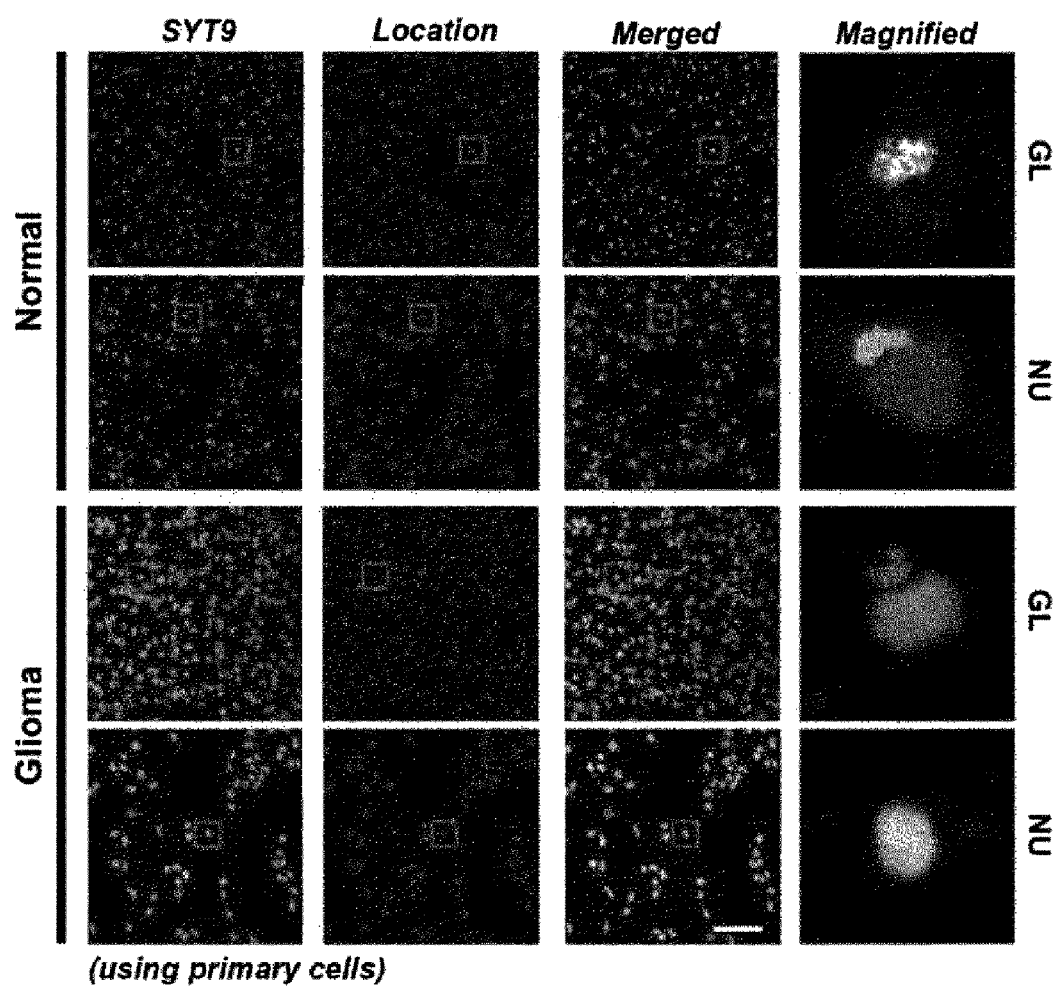
(using primary cells)

METHOD FOR DIAGNOSING GLIOMA AND SCREENING FOR THE THERAPEUTICS OF GLIOMA THROUGH IDENTIFYING PROTEIN RELOCATION

CROSS-REFERENCE TO RELATED APPLICATIONS

This application is a continuation-in-part of PCT International Application No. PCT/KR2012/003110, filed Apr. 23, 2012, claiming priority of Korean Patent Application No. 10-2011-0037728, filed Apr. 22, 2011, the contents of each of which are hereby incorporated by reference in their entirety.

BACKGROUND OF THE INVENTION

1. Field of the Invention

The present invention relates to a method for diagnosing glioma by comparing the protein locations in an individual to be diagnosed with those of the normal control nerve cells. More particularly, the present invention relates to a method for diagnosing glioma comprising determining that an individual has glioma or of predicting prognosis after surgery of glioma when the expression level of GFRα4 in the endoplasmic reticulum is higher than that in the plasma membrane, and a method for screening a therapeutic agent for glioma. Further, the present invention relates to a method for diagnosing glioma or for predicting prognosis after surgery of glioma based on the number of GFRα4 and PSPN interactions.

2. Description of the Related Art

A change in the subcellular location of a protein is fundamental to cell function and regulatory control. Generally, protein location can be governed by signal peptides, which convey proteins to the specific organelle. It is also an important regulatory mechanism, as signal peptides can be modified by carrier proteins that recognize a particular pattern of modifications after translation of mRNA into peptide. For example, STAT3 (signal transducer and activator of transcription 3) is phosphorylated by various cytokines and growth signals, resulting in its relocation to the nucleus, where it serves as a strong DNA-binding transcriptional activator. Inappropriate phosphorylation and relocation of STAT3 are known to promote oncogenesis through abnormal cell cycle progression, angiogenesis, and invasion of tissue. Changes in protein location are also associated with genetic disorders. For instance, in Zellweger syndrome, relocation of peroxisomal proteins leads to dysfunctional fatty acid oxidation.

Therefore, functional changes of cells can be predicted through accurate identification of changes in the subcellular locations of proteins and the type of neighboring proteins.

Meanwhile, there are two types of brain tumors; primary brain tumors that originate in the brain itself and metastatic brain tumors that spread from other organs. Primary brain tumors can be further divided into two types of tumors—benign and malignant. Even if primary brain tumors are benign, benign tumors can compress normal parts of the brain, causing severe nerve dysfunction. In many cases, benign brain tumors are also difficult to treat, like malignant tumors. Each year, over 190,000 people in the United States and 10,000 people in Canada are diagnosed with a primary or metastatic brain tumor. Brain tumors are the leading cause of solid cancer death in children under the age of 20. Although, brain tumors can be benign, the survival rate is lower than that of breast cancer. The incidence of metastatic brain tumors is estimated to be 10-15%, but it is growing with the increasing survival rate of tumor patients. At present, the prevalence rate in the United States is estimated to be 29.5 per 100,000, and glioma accounts for 50% of all brain tumors. Glial cells exist between the neurons and between the neuron and the blood vessel, and function to supply nutrients or oxygen to neurons. Many gliomas are malignant, and classified by the cell type or their features.

Gliomas are the most common type of primary brain tumor, and are associated with poor prognosis. High-grade astrocytomas including glioblastoma multiforme (GBM) and anaplastic astrocytoma (AA) are the most common intrinsic brain tumor m adults. While there has been progress in understanding the molecular genetics of high-grade astrocytomas, the cell type(s) of origin are still uncertain, and the molecular determinants of the disease's aggressiveness are not well understood. A better understanding of the cellular origin and molecular pathogenesis of these tumors may identify new targets for treatment of these neoplasms that are nearly uniformly fatal.

The grading of tumors is often critical to obtain an accurate diagnosis and prognosis of disease progression, and glioma is no exception. Decades of experience have led to a system of diagnosis of gliomas based on histology. Gliomas are histologically defined by whether they exhibit primarily astrocytic or oligodendroglial morphology. Gliomas are graded by cellularity, nuclear atypia, necrosis, mitotic figures, and microvascular proliferation, and all features associated with biologically aggressive behavior. This system of diagnosis has been developed over decades of clinical experience with gliomas and has now become the cornerstone of neuro-oncology [Kleihues, P. et al., World Health Organization ("WHO") classification of tumors, Cancer 88: 2887 (2000)].

Satisfactory studies to develop an early, accurate and simple diagnosis of glioma with poor prognosis have not been conducted yet. Accordingly, the present inventors have made many efforts to develop an accurate diagnostic method for glioma. As a result, they found that locations of particular proteins and the number of protein-protein interactions differ between normal cells and glioma cells, which were visualized by FCCS (fluorescence cross-correlation spectroscopy), and glioma can be diagnosed by comparing the expression levels in the subcellular locations between normal cells and glioma cells through Western blotting, thereby completing the present invention.

SUMMARY OF THE INVENTION

An object of the present invention is to provide a method for diagnosing glioma by comparing the subcellular locations and interaction of proteins of an individual to be diagnosed.

Another object of the present invention is to provide a method for screening a therapeutic agent for glioma.

BRIEF DESCRIPTION OF THE DRAWINGS

In FIG. 1, A-F, G-L and M-R are confocal images (green) for PSPN, GFRα4, and RET together with markers (red) for the plasma membrane and endoplasmic reticulum, respectively.

FIG. 9b shows conditional changes in the subcellular location of RNF138. The upper panel shows the percentage of proteins in the endoplasmic reticulum and the nucleus by a high content screening method (Thermo Fisher Scientific Inc.). The lower panel shows RNF138 locations in normal cells and glioma cells by Western blot.

FIG. 12b shows conditional changes in the subcellular location of DIP2A. Overlap between DIP2A and the nucleus marker or the endoplasmic reticulum marker was examined in normal cells and glioma cells.

FIG. 14a shows changes in the subcellular location of DLX2 during glioma progression, and shows confocal images for DLX2 relocation in normal cells, low-grade glioma cells and high-grade glioma cells. DLX2 relocated from the endoplasmic reticulum (ER) to the nucleus (NU) with glioma progression.

FIG. 14b shows conditional changes in the subcellular location of DLX2. Overlap between DLX2 and the endoplasmic reticulum marker or the nucleus marker was examined in normal cells and glioma cells.

FIG. 15b shows conditional changes in the subcellular location of TBX19. Overlap between TBX19 and the endoplasmic reticulum marker or the nucleus marker was examined in normal cells and glioma cells.

FIG. 17b shows conditional changes in the subcellular location of CPB1. Overlap between CPB1 and the cytosol marker or the endoplasmic reticulum marker was examined in normal cells and glioma cells.

FIG. 19a shows changes in the subcellular location of ARHGEF15 during glioma progression, and shows confocal images for ARHGEF15 relocation in normal cells, low-grade glioma cells and high-grade glioma cells. ARHGEF15 relocated from the endoplasmic reticulum (ER) to the plasma membrane (PM) with glioma progression.

FIG. 19b shows conditional changes in the subcellular location of ARHGEF15. Overlap between ARHGEF15 and the endoplasmic reticulum marker or the plasma membrane marker was examined in normal cells and glioma cells.

FIG. 20b shows conditional changes in the subcellular location of CLK2. Overlap between CLK2 and the endoplasmic reticulum marker or the nucleus marker was examined in normal cells and glioma cells.

FIG. 20c shows conditional changes in the subcellular location of CLK2. The upper panel shows the percentage of proteins in the endoplasmic reticulum and the nucleus, and the lower panel shows CLK2 locations in normal cells and glioma cells by Western blot.

FIG. 21b shows conditional changes in the subcellular location of SYT9. Overlap between SYT9 and the Golgi apparatus marker or the nucleus marker was examined in normal cells and glioma cells.

DETAILED DESCRIPTION OF THE PREFERRED EMBODIMENTS

Figure 1:
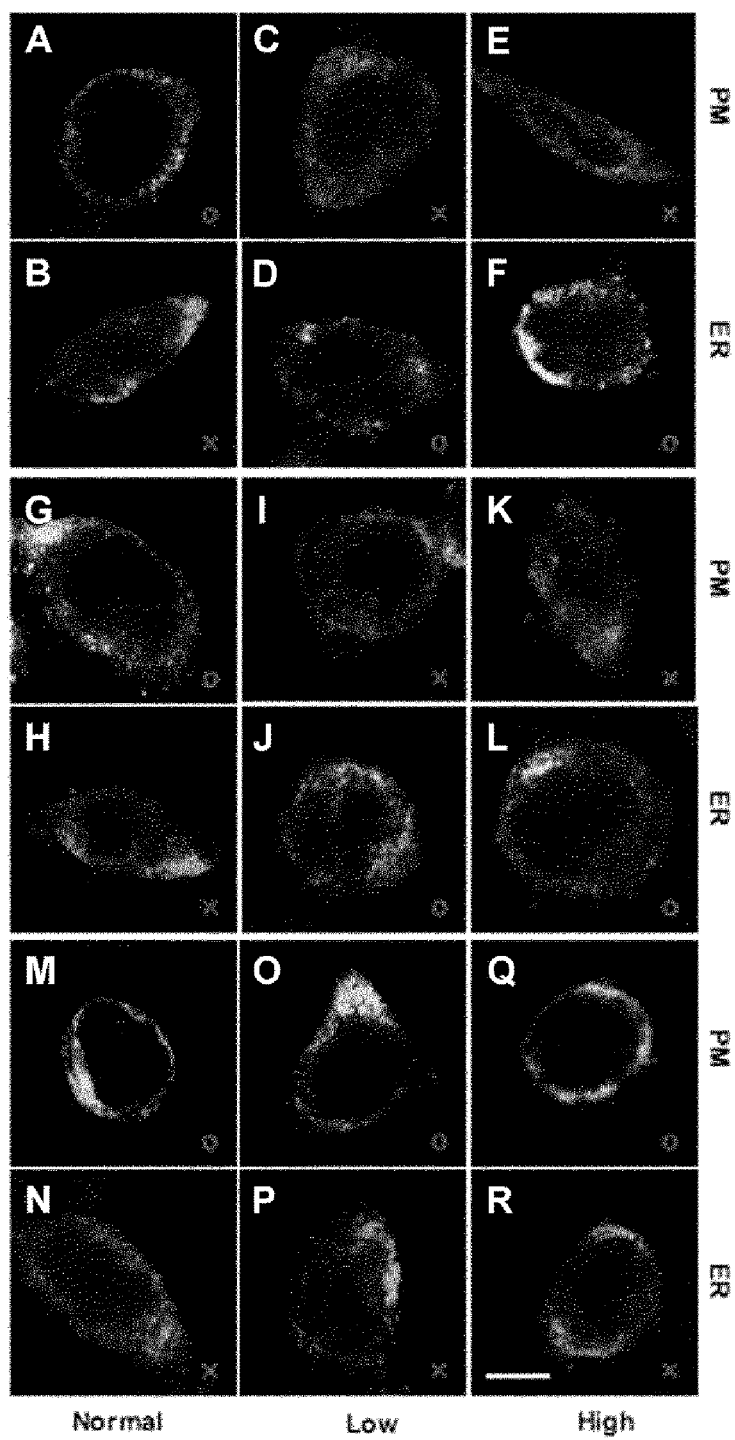
FIG. 1 shows conditional changes in the subcellular locations of PSPN, GFRα4 and RET. In glioma cells, relocations of PSPN and GFRα4 from the plasma membrane to the endoplasmic reticulum were observed, whereas RET remains in the plasma membrane regardless of conditions.

In one aspect, the present invention provides a method for diagnosing glioma, comprising measuring the expression levels of GFRα4 (GDNF receptor alpha 4) in the plasma membrane and endoplasmic reticulum of the cells isolated from an individual to be diagnosed; and comparing the GFRα4 expression levels between the endoplasmic reticulum and the plasma membrane in the individual to be diagnosed. If its expression level in the endoplasmic reticulum is higher than that in the plasma membrane, the individual can be diagnosed to have glioma.

The above method may further comprise examining whether the PSPN (persephin) expression level in the endoplasmic reticulum is higher than that in the plasma membrane in the cells isolated from the individual to be diagnosed.

In one embodiment of the present invention, in vivo fluorescence imaging of normal cells and glioma cells was performed by FCCS (fluorescence cross-correlation spectroscopy) or the like. As a result, it was found that PSPN and GFRα4 are located in the plasma membrane of normal cells, whereas they mislocate to the endoplasmic reticulum of glioma cells. The expression levels of PSPN and GFRα4 in the plasma membrane and the endoplasmic reticulum of normal cells and glioma cells were compared by Western blot. As a result, in glioma cells, their expression levels in the endoplasmic reticulum were found to be higher than those in the plasma membrane (Example 9).

GFRα4 is GDNF receptor alpha 4 which is known to bind with RET proto-oncogene, and is identified by Genbank Accession Nos. AAG25925, NM_145762, and AF253318. Such GFRα4 includes all of the derivatives or fragments thereof having homology thereto, as long as they can be used for glioma diagnosis.

Further, in the step of measuring the GFRα4 expression levels in the plasma membrane and the endoplasmic reticulum, the step of measuring the PSPN protein expression levels in the plasma membrane and the endoplasmic reticulum may be further carried out. PSPN is a glial cell line-derived neurotrophic factor (GDNF) family ligand which facilitates neuron survival through binding to GFRα4, and is identified by Genbank Accession Nos. AAC39640, NM_004158, and AF040962.

Further, the method for diagnosing glioma may further comprise examining the subcellular locations of one or more proteins selected from the group consisting of KIF13A (kinesin family member 13A), RNF138 (E3 ubiquitin ligase), TLX3 (T-cell leukemia homeobox protein 3), ATIC (5-aminoimidazole-4-carboxamide ribonucleotide formyltransferase/IMP cyclohydrolase), DIP2A (DIP2 disco-interacting protein 2 homolog A), STAT3 (signal transducer and activator of transcription 3), DLX2 (distal-less homeobox 2), TBX19 (T-box 19), AGAP1 (ArfGAP with GTPase domain, ankyrin repeat and PK domain 1), CPB1 (carboxypeptidase B1), NFRκB (nuclear factor related to kappaB binding protein), ARHGEF15 (Rho guanine nucleotide exchange factor 15), CLK2 (CDC-like kinase 2), and SYT9 (synaptotagmin IX) of the individual to be diagnosed by comparing their expression levels.

In one embodiment of the present invention, in vivo imaging confirmed relocation of KIF13A from the Golgi apparatus to the nucleus during glioma progression (Example 13). In vivo imaging also confirmed that in normal cells, RNF138 overlaps with markers for the endoplasmic reticulum, while in glioma cells RNF138 overlaps with markers for the nucleus, indicating relocation of RNF138 from the endoplasmic reticulum to the nucleus during glioma progression. Furthermore, relocation of TLX3 (T-cell leukemia homeobox 3), which is a member of a family of orphan homeobox genes encoding DNA-binding nuclear transcription factors, from the nucleus to the endoplasmic reticulum during glioma progression was also confirmed (Example 14).

In the Examples of the present invention, it was also confirmed that the locations of one or more proteins selected from the group consisting of ATIC, DIP2A, STAT3, DLX2, TBX19, AGAP1, CPB1, NFRκB, ARHGEF15, CLK2 and SYT9 differed between normal cells and glioma cells, in addition to the above proteins. Specifically, during glioma progression, relocation of ATIC from the cytosol (CY) to the nucleus (NU), relocation of DIP2A from the nucleus (NU) to the endoplasmic reticulum (ER), relocation of STAT3 from the plasma membrane (PM) to the nucleus (NU), relocation of DLX2 from the endoplasmic reticulum (ER) to the nucleus (NU), relocation of TBX19 from the endoplasmic reticulum (ER) to the nucleus (NU), relocation of AGAP1 from the cytosol (CY) to the Golgi apparatus (GL), relocation of CPB1 from the cytosol (CY) to the endoplasmic reticulum (ER), relocation of NFRκB from the endoplasmic reticulum (ER) to the nucleus (NU), relocation of ARKGEF15 from the endoplasmic reticulum (ER) to the plasma membrane (PM), relocation of CLK2 from the endoplasmic reticulum (ER) to the nucleus (NU), and relocation of SYT9 from the Golgi apparatus (GL) to the nucleus (NU) were observed (Example 15).

As such, it was found that location information of the proteins, KIF13A (Genbank No.: CAC20442, AJ291578), RNF138 (Genbank No.: AAD46623, NM_016271, AF162680), TLX3 (Genbank No.: CAA11550, AJ223798), ATIC (Genbank No.: NP_004035, NM_004044), DIP2A (Genbank No.: AAM18046, NM_015151, AF490768), STAT3 (Genbank No.: AAH14482, NM_139276, NM_003150, BC014482), DLX2 (Genbank No.: AAB40902, U51003), TBX19 (Genbank No.: CAB37936, NM_005149, AJ010277), AGAP1 (Genbank No.: AAL04172, NM_014914, AF413078), CPB1 (Genbank No.: CAA12163, AJ224866), NFRκB (Genbank No.: NP_006156, NM_006165), ARHGEF15 (Genbank No.: BAA74938, NM_173728, A3020722), CLK2 (Genbank No.: AAA61482, NM_003993, L29218) and SYT9 (Genbank No.: 3AG51449, NM_175733, AK055003) is also changed in glioma.

Based on the above Example, the method for diagnosing glioma of the present invention may further comprise examining whether one or more proteins selected from the group consisting of KIF13A and SYT9 of an individual to be diagnosed show higher expression levels in the nucleus than in the Golgi apparatus.

Also, the method may further comprise examining whether one or more proteins selected from the group consisting of RNF138, BLX2, TBX19 and NFRκB of an individual to be diagnosed show higher expression levels in the nucleus than in the endoplasmic reticulum.

Also, the method may further comprise examining whether one or more proteins selected from the group consisting of TLX3 and DIP2A of an individual to be diagnosed show higher expression levels in the endoplasmic reticulum than in the nucleus, and examining whether ATIC of an individual to be diagnosed shows higher expression level in the nucleus than in the cytosol.

Also, the method may further comprise examining whether STAT3 of an individual to be diagnosed shows higher expression level in the nucleus than in the plasma membrane, and examining whether AGAP1 of an individual to be diagnosed shows higher expression level in the Golgi apparatus than in the cytosol.

Also, the method may further comprise examining whether CPB1 of an individual to be diagnosed shows higher expression level in the endoplasmic reticulum than in the cytosol.

Also, the method may further comprise examining whether ARHGEF15 of an individual to be diagnosed shows higher expression level in the plasma membrane than in the endoplasmic reticulum.

As used herein, the term "glioma" refers to a tumor that arises from glial cells or their precursors of the brain or spinal cord. Further, "diagnosis" means to verify the existence, prognosis or characteristics of the pathological state. With respect to the purposes of the present invention, diagnosis means to identify glioma tumor, to determine its unique features or to predict prognosis after treatment such as surgery.

As used herein, the term "individual to be diagnosed" includes a subject having glioma or being susceptible to glioma, and it may be a mammal. Preferred examples of the mammal may include human, non-human primates, mouse, rat, dog, cat, horse and cattle, but are not limited thereto.

In embodiments of the present invention, a biological sample can be collected from the individual to be diagnosed, and therefore, locations of the proteins that differ between the glioma cells and normal cells and their expression levels in a particular location can be measured. The biological sample includes body's tissues, body fluid, blood, serum, cell or the like, but is not limited thereto. In the preferred Example, the biological sample is a nerve cell. In addition, the cell is purified from the obtained body's tissue and body fluid, and used as the biological sample.

In the present invention, to measure a change in the location of each protein, protein expression in the subcellular location can be measured by any method known in the art. For example, the presence and expression of each protein in the subcellular location can be confirmed by contacting each protein with a specific antibody and then examining formation of antigen-antibody complex. As used herein, the term "antigen-antibody complex" refers to a binding product of a particular protein in the biological sample with an antibody specifically recognizing the protein.

As used herein, the term "antibody" means a specific protein molecule that is directed against an antigenic region. The antibody used in the present invention may be a monoclonal or polyclonal antibody, an immunologically active fragment (e.g., Fab or (Fab)$_2$ fragment), an antibody heavy chain, a humanized antibody, an antibody light chain, a genetically engineered single chain Fv molecule, a chimeric antibody or the like. Since the proteins for glioma diagnosis of the present invention are the known proteins, the antibodies used in the present invention can be prepared using the known proteins as antigens by the method widely known in the immunological fields. The protein used as the antigen of the antibody according to the present invention can be extracted from natural sources or synthesized, and prepared by a recombination method, based on DNA sequence. If the recombinant DNA technology is used, a nucleic acid encoding the protein is inserted into a proper expression vector, and host cells are cultured to express the desired protein in the transformant that is transformed with the recombinant expression vector, and then the desired protein is recovered from the transformant.

Methods for measuring the protein level are exemplified by Western blotting, ELISA, radioimmunoassay, radioimmunodiffusion, Ouchterlony immunodiffusion, rocket immunoelectrophoresis, immunohistostaining, immunoprecipitation, complement fixation test, FACS, and protein chip assay, but not limited thereto.

Further, FCS, FCCS or the like can be used as a method for identifying the presence of a protein in a particular location through in vivo imaging.

In the method for diagnosing glioma by identifying the subcellular locations of the proteins, measuring the protein expression level is performed by using a isolated antibody being specific to the protein.

The method for diagnosing glioma by identifying the subcellular locations of the proteins may further comprise measuring the number of GFRα4 and RET interactions and the number of PSPN and RET interactions in an individual to be diagnosed to compare them with those of the control group; and determining the glioma as a higher grade glioma when the number of GFRα4 and RET interactions and the number of PSPN and RET interactions in the individual to be diagnosed are lower than those of the control group.

As used herein, the term "control group" means a normal individual having no glioma.

In one embodiment of the present invention, changes in the number of interactions during glioma, progression were examined by measuring the number of interactions between RET/GFRα4/PSPN proteins (Example 10). The normal brain tissue showed a high number of interactions between RET and GFRα4 or PSPN whereas the numbers of interactions between GFRα4 and RET, and PSPN and RET were reduced with glioma progression. That is, as PSPN and GFRα4 relocated to the endoplasmic reticulum during glioma progression, the number of interactions with RET were reduced and the number of interactions between PSPN and GFRα4 were increased with glioma progression.

The diagnostic method of the present invention may be a method for predicting prognosis after glioma surgery, comprising measuring the GFRα4 (GDNF receptor alpha 4) expression levels in the plasma membrane and the endoplasmic reticulum of the cells isolated from the individual to be diagnosed; and examining whether the GFRα4 expression level in the endoplasmic reticulum is higher than that in the plasma membrane of the cells isolated from the individual to be diagnosed. That is, when the GFRα4 expression level in the endoplasmic reticulum is higher than that in the plasma membrane of the cells isolated from the individual to be diagnosed, it can be predicted that the individual has poor prognosis after glioma surgery.

In the above method, the method may further comprise measuring the number of interactions between GFRα4 and PSPN in the cells isolated from an individual to be diagnosed to compare it with that of the control group; and examining whether the number of interactions between GFRα4 and PSPN in the cells isolated from an individual to be diagnosed is higher than that of the control group. That is, when the number of interactions between GFRα4 and PSPN is higher than that of the control group, it can be predicted that the individual has poor prognosis after glioma surgery.

In one embodiment of the present invention, postoperative prognosis was examined by eosin staining of the tissue of a patient after glioma surgery in order to examine a correlation between changes in the GFRα4 location in the patient after glioma surgery and prognosis after glioma surgery. As a result, as prognosis after glioma surgery was poorer, GFRα4 relocated from the plasma membrane to the endoplasmic reticulum, indicating that prognosis after glioma surgery can be predicted by examining changes in the GFRα4 location (Example 16).

Further, a correlation between changes in the number of interactions between PSPN and GFRα4 in the patient after glioma surgery and prognosis after glioma surgery was examined. As a result, as prognosis after glioma surgery was poorer, higher number of interactions between PSPN and GFRα4 was observed. Further, it was confirmed that the result of predicting prognosis after glioma surgery by examining the number of interactions between PSPN and GFRα4 is associated with survival rate after surgery, indicating that prognosis after glioma surgery can be predicted by examining changes in the number of interactions between PSPN and GFRα4 (Example 17).

In another aspect, the present invention provides a method for screening a therapeutic agent for glioma.

In detail, the method comprises treating nerve cells with a candidate therapeutic agent for glioma; and comparing its inhibition of GFRα4 expression with that of the control group that is treated, with no candidate therapeutic agent.

Specifically, a method of comparing an increase or decrease in GFRα4 expression in the presence or absence of the candidate therapeutic agent for glioma can be used for screening the therapeutic agent for glioma. If a decrease in GFRα4 expression is observed, the candidate material can be determined, as the therapeutic agent for glioma.

As used herein, the term "candidate material" includes materials capable of treating glioma without limitation, and examples thereof may include chemicals, siRNAs, antisense oligonucleotides, antibodies or the like.

In one embodiment of the present invention, it was found that GFRα4 is involved in cell proliferation, and inhibition of GFRα4 activity leads to reduction of the transcription factor STAT3 showing high levels of activity in cancer (Example 11), suggesting that glioma can be treated by inhibiting GFRα4 expression, and a therapeutic agent for glioma capable of inhibiting GFRα4 expression can be also screened.

Further, glioma proliferation can be remarkably reduced by GFRα4 relocation from the endoplasmic reticulum to the plasma membrane (Example 12), suggesting that glioma can be treated by relocation of GFRα4 as in normal cells.

In still another aspect, the present invention provides a composition for diagnosing glioma. Specifically, it may comprise an agent for measuring the expression level of a particular protein showing different subcellular locations between normal cells and glioma cells in the cells isolated from an individual to be diagnosed or in the cultured cells. The subcellular locations include nuclear membrane, plasma membrane, endoplasmic reticulum, nucleoplasm, cytosol, Golgi apparatus, subcellular organelles or the like without limitation, but may be selected depending on the type of the desired protein.

The agent for measuring the protein expression level may be required for Western blot, cell fraction, immunochemical staining, ELISA which are generally used in the art to identify protein expressions. In particular, the agent may be an agent for identifying subcellular location.

Specifically, the composition may include an agent for measuring the GFRα4 expression level in isolated cells, and in particular, further include an agent for measuring the expression levels of one or more proteins selected from the group consisting of PSPN, KIF13A (kinesin family member 13A), RNF138 (E3 ubiquitin ligase), TLX3 (T-cell leukemia homeobox protein 3), ATIC (5-aminoimidazole-4-carboxamide ribonucleotide formyltransferase/IMP cyclohydrolase), DIP2A (DIP2 disco-interacting protein 2 homolog A), STAT3 (signal transducer and activator of transcription 3), DLX2 (distal-less homeobox 2), TBX19 (T-box 19), AGAP1 (Arf-GAP with GTPase domain, ankyrin repeat and PH domain 1), CPB1 (carboxypeptidase B1), NFRκB (nuclear factor related to kappaB binding protein), ARHGEF15 (Rho guanine nucleotide exchange factor 15), CLK2 (CDC-like kinase 2), and SYT9 (synaptotagmin IX).

In still another aspect, the present invention provides a kit comprising the composition for diagnosing glioma of the present invention. The kit may be used tor tissue staining, cell staining, cell fraction, Western blot or the like.

Hereinafter, the present invention will be described in more detail with reference to Examples. However, these Examples are for illustrative purposes only, and the invention is not intended to be limited by these Examples.

Example 1

Identification of Static Locations of Proteins

For known static locations of human proteins, GO Cellular Component annotations were obtained using the AmiGO tool (http://amigo.geneontology.org/cgi-bin/amigo/go.cgi). Sequence information of each protein was obtained using the UniProt database, and the known protein-protein interaction network information was obtained from the HPRD, BIND, REACTOME, and DIP databases.

Expression profiles of normal brain and low- and high-grade gliomas were obtained from the GEO database.

Example 2

Brain Tissue Preparation and Primary Cell Culture

Human normal brain and glioma tissues were acquired from the Brain Bank of Seoul National University Hospital. Brain tissues were fixed in 4% paraformaldehyde in 0.1 M phosphate buffer, followed by cryoprotection in 30% sucrose overnight. Three micron sections were prepared on a cryostat (Leica). Primary cells were prepared directly from human normal brain and glioma tissues.

Example 3

Immunohistochemistry

Tissue sections were incubated overnight with protein-specific antibodies at 4° C., and then rinsed with PBS and incubated for 1 hour at room temperature with secondary antibodies. For counterstaining of the nucleus, cells were incubated with DAPI (4'6-diamidino-2-phenylindole; 1 µg/ml, Sigma Aldrich) for 40 seconds. After washing with PBS, coverslips were mounted on glass slides using VectaShield mounting media (Vector Laboratories), and analyzed using an LSM 710 confocal microscope (Carl Zeiss).

Example 4

Proximity Ligation Assay (PLA)

A proximity ligation assay (PLA) was performed in both primary cells and tissues to visualize protein-protein interactions. Tissues were washed with chilled PBS and incubated, overnight with protein-specific antibodies at 4° C. PLA was performed according to the method known in the art using the Duolink detection kit (Olink Bioscience). Specimens were analyzed using an LSM 710 confocal microscope (Carl Zeiss).

The number of in situ PLA signals per cell was counted by semiautomated image analysis using BlobFinder V3.0.

Example 5

Live Cell Imaging and FCS and FCCS Measurements

SM510/ConfoCor2 and LSM710/Confocor3 (Carl Zeiss Inc.) were used for live cell imaging, FCS (Fluorescence Correlation Spectroscopy) and FCCS (Fluorescence cross-correlation spectroscopy) measurements to analyze colocalization and interactions between proteins in live primary cells.

Data was analyzed with the ConfoCor2/Confocor3 software as described in the previous study (Pack et al., 2006 Microenvironment and effect of energy depletion in the nucleus analyzed by mobility of multiple oligomeric EGFPs. Biophys J 91, 3921-3936; Noda et al., 2008 Reciprocal interaction with G-actin and tropomyosin is essential for aquaporin-2 trafficking. J Cell Biol 182, 587-601).

Example 6

Transfection and sirNA Synthesis

Human glioma primary cells were transfected using the OneDrop Microporator MP kit (NanoEnTek) after siRNA synthesis according to the method known in the art.

Example 7

Immunoblot

Cell lysates were prepared with lysis buffer containing 7 M urea, 2 M thiourea, and 4% CHAPS. Equal amounts (25 µg) of protein from each group were separated in 12% polyacrylamide gels (Invitrogen) and transferred to a nitrocellulose membrane (Millipore). Proteins were detected with protein-specific antibodies.

Example 8

Imaging of Signal Transduction by FKBF-Rapamycin-FRB

Human glioma primary cells were transfected with siGFRα4 and then transfected with fusion vectors of RET-FRB and FKBP-GFRα4. Cells were incubated at room temperature for 20 min with 1 nmol/L of rapamycin and evaluated in a growth/proliferation assay.

Example 9

Relocation of PSPN and GFRα4 During Glioma Progression

It was examined whether the two proteins of PSPN (persephin) and GFRα4 (GDNF receptor alpha 4) relocate from the plasma membrane (PM) to the endoplasmic reticulum (ER) during glioma progression.

PSPN is a glial cell line-derived neurotrophic factor (GDNF) family ligand which facilitates neuron survival through binding to GFRα4.

GFRα4 is known to bind with RET proto-oncogene.

In the present invention, in vivo fluorescence imaging showed that PSPN and GFRα4 are located in the plasma membrane of normal cells, but relocate to the endoplasmic reticulum in glioma (FIGS. 1A-1L). These results were observed in a large population of primary glioma cells (65% or more of the cells). In addition, the RET proto-oncogene was found to locate in the plasma membrane in both normal cells and glioma cells (FIGS. 1M-1R).

Figure 2:
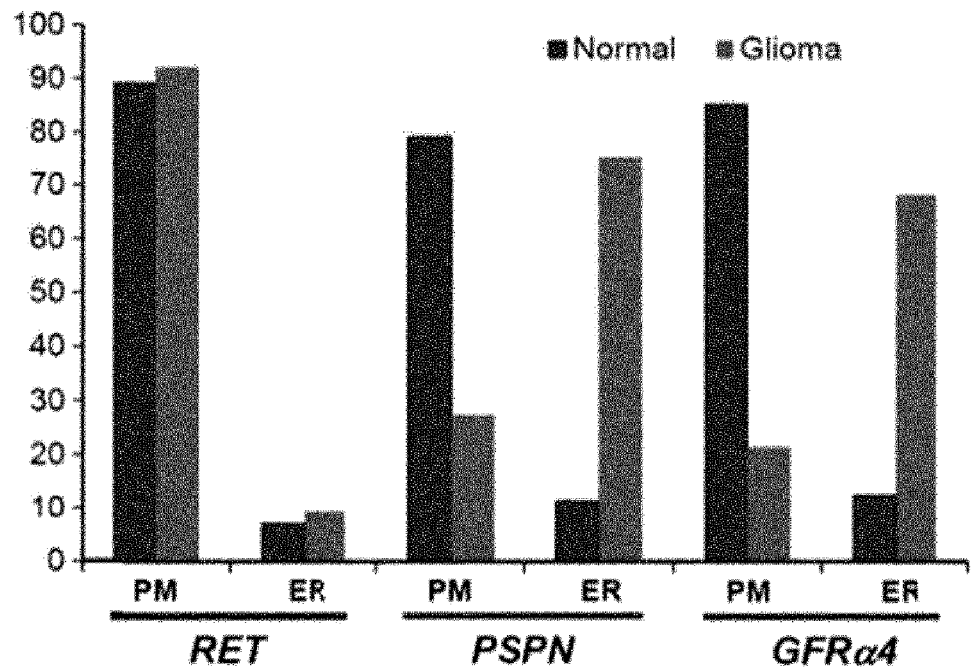
FIG. 2 shows the results of measuring the presence of RET, PSPN and GFRα4 in the plasma membrane and the endoplasmic reticulum of glioma cells and normal cells.
Figure 3:
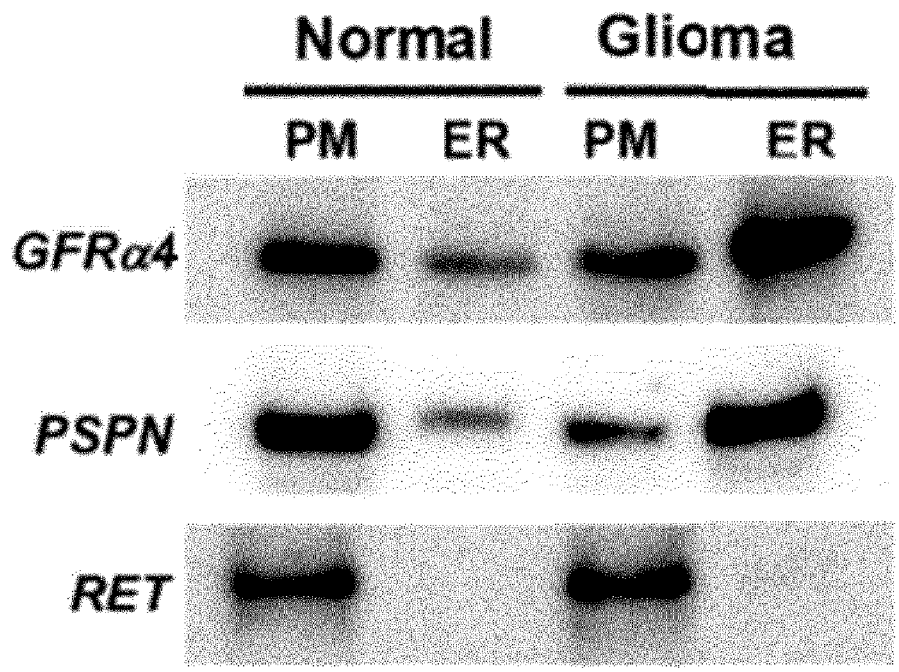
FIG. 3 shows the results of Western blot to identify the locations of RET, PSPN and GFRα4 in normal cells and glioma cells.

Furthermore, the presences of RET, PSPN and GFRα4 in the plasma membrane and endoplasmic reticulum were examined in glioma cells and normal cells. As a result, approximately 80-90% of normal cells showed the presence of RET, PSPN and GFRα4 in the plasma membrane, whereas most glioma cells showed the presence of PSPN and GFRα4 (approximately 70%) in the endoplasmic reticulum, and the presence of RET (approximately 90%) in the plasma membrane (FIG. 2). The results of Western blot to identify the locations of RET, PSPN and GFRα4 in normal cells and glioma cells are shown in FIG. 3.

These results confirmed that PSPN and GFRα4 relocates from the plasma membrane to the endoplasmic reticulum during glioma progression, and RET remains in the plasma membrane.

Example 10

Changes in the Number of Interactions Between PSPN and GFRα4 in Glioma

Figure 4:
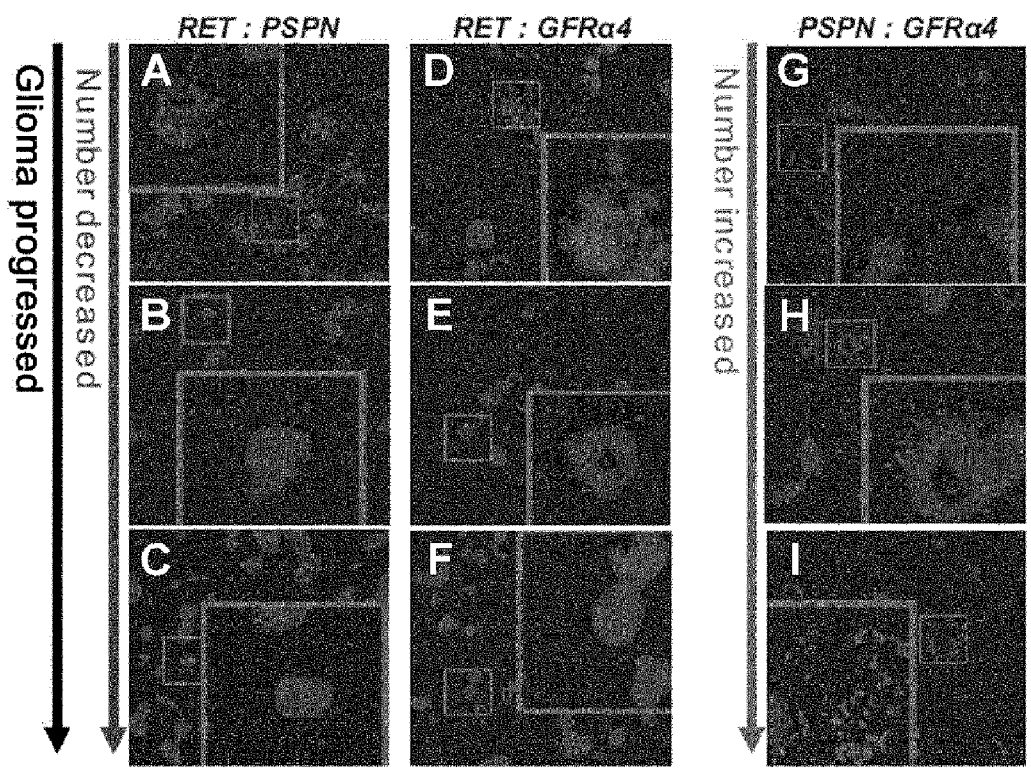
FIGS. 4A-I shows the numbers of physical interactions between RET and PSPN (A-C), RET and GFRα4 (D-F), and PSPN and GFRα4 (G-I) by proximity ligation assay.

The results of proximity ligation assay showed a high number of interactions between RET and GFRα4 or PSPN in the normal brain cells (FIGS. 4A and 4D). However, the number of interactions was reduced approximately 6-7 fold in low-grade glioma (FIGS. 4B, 4C, 4E, 4F). The reduction in the number of interactions is attributed not to reduced expression levels of RET/GFRα4/PSPN but to shift of PSPN and GFRα4 to the endoplasmic reticulum during glioma progression. In contrast, the number of interactions between PSPN and GFRα4 was increased with glioma progression (FIGS. 4G-4I).

Example 11

Regulation of Cell Proliferation and STAT3 Expression by GFRα4

In order to examine the effect of GFRα4 on proliferation of glioma cells, [3H] thymidine incorporation assay was performed in high-grade glioma cells with or without GFRα4 silencing. Thymidine incorporation was rapidly reduced approximately 8-fold after GFRα4 silencing, indicating that GFRα4 is involved in cell proliferation (FIG. 5) and proliferation of glioma cells can be inhibited by inhibition of GFRα4 activity.

Figure 5:
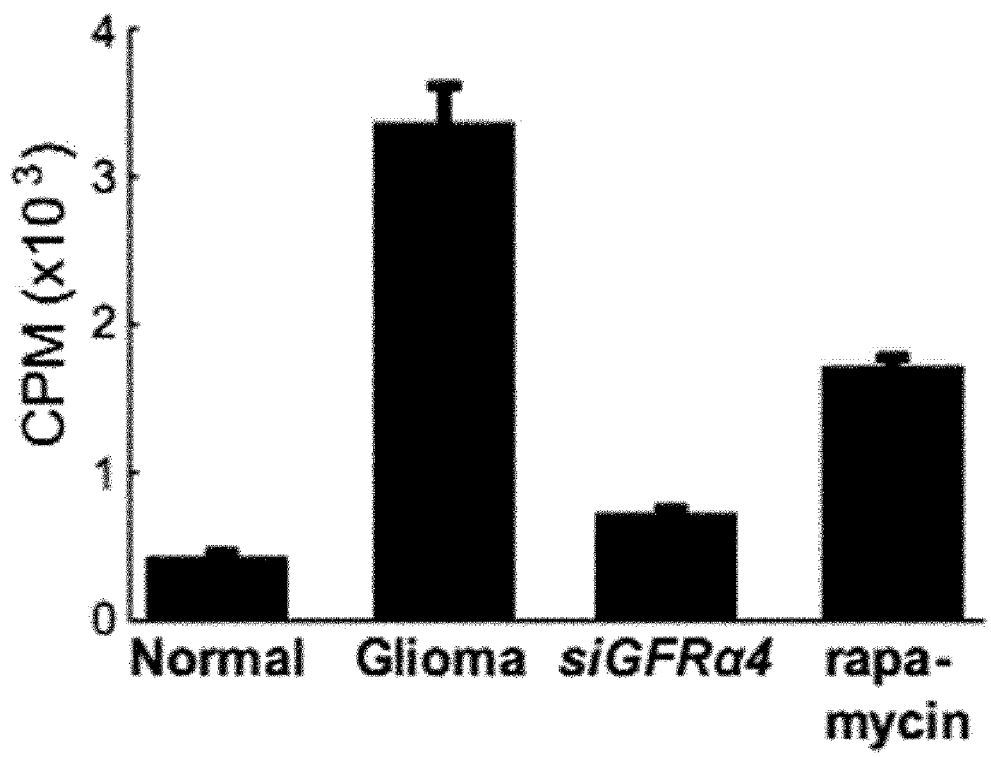
FIG. 5 is the result of [3H] thymidine incorporation assay in order to examine the effect of GFRα4 on proliferation of glioma cells, and is the result of Western blot showing the reduced amount of STAT3 after GFRα4 silencing.
Figure 5:

Further, the effect of GFRα4 on STAT3 which is a transcription factor showing high activity in cancer was examined. STAT3 locates in the plasma membrane of the normal brain, but relocates to the nucleus in the glioma tissue. The number of interactions between STAT3 and GFRα4 was analyzed by proximity ligation assay. The number of interactions between STAT3 and GFRα4 was reduced in glioma, compared to the normal tissue. The results of Western blot showed that the amount of STAT3 was reduced in high-grade glioma 74 hours after GFRα4 silencing (FIG. 5).

Example 12

Effect of GFRα4 Relocation on Proliferation of Glioma Cells

It was examined whether the GFRα4 relocation from the endoplasmic reticulum to the plasma membrane is directly associated with proliferation of glioma cells.

Figure 6:
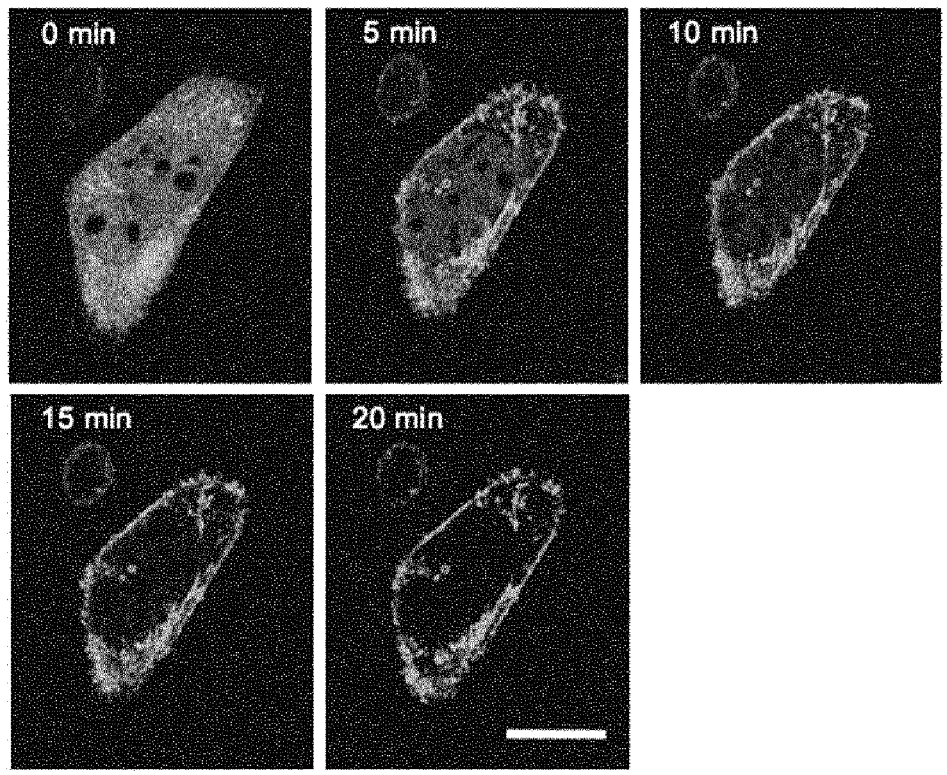
FIG. 6 shows the result of successful GFRα4 relocation from the endoplasmic reticulum to the plasma membrane in glioma cells.
Figure 7:
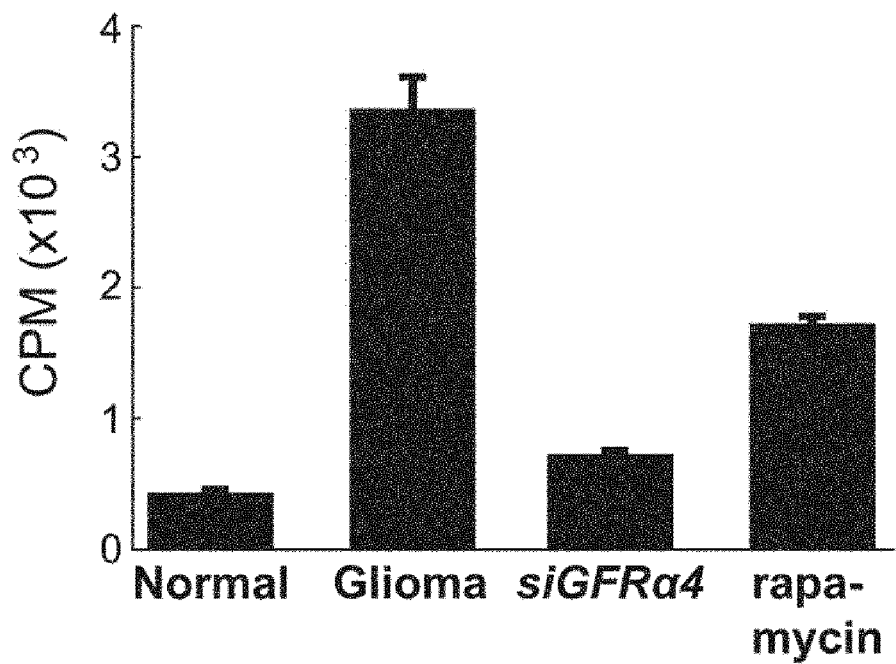
FIG. 7 shows a remarkable reduction in cell proliferation after GFRα4 relocation.

FRBP-GFRα4 and FKB-RET were transfected by dimerization of FRBP-rapamycin-FKB, and GFRα4 relocation from the endoplasmic reticulum to the plasma membrane was confirmed (FIG. 6). Proliferation assay was performed after GFRα4 relocation. As a result, cell proliferation was found to remarkably reduce (from $3.3 \times 10^3$ CPM to $1.8 \times 10^3$) (FIG. 7). These results indicate that changes in the subcellular location of GFRα4 in glioma greatly affect proliferation of cancer cells.

Example 13

Figure 8:
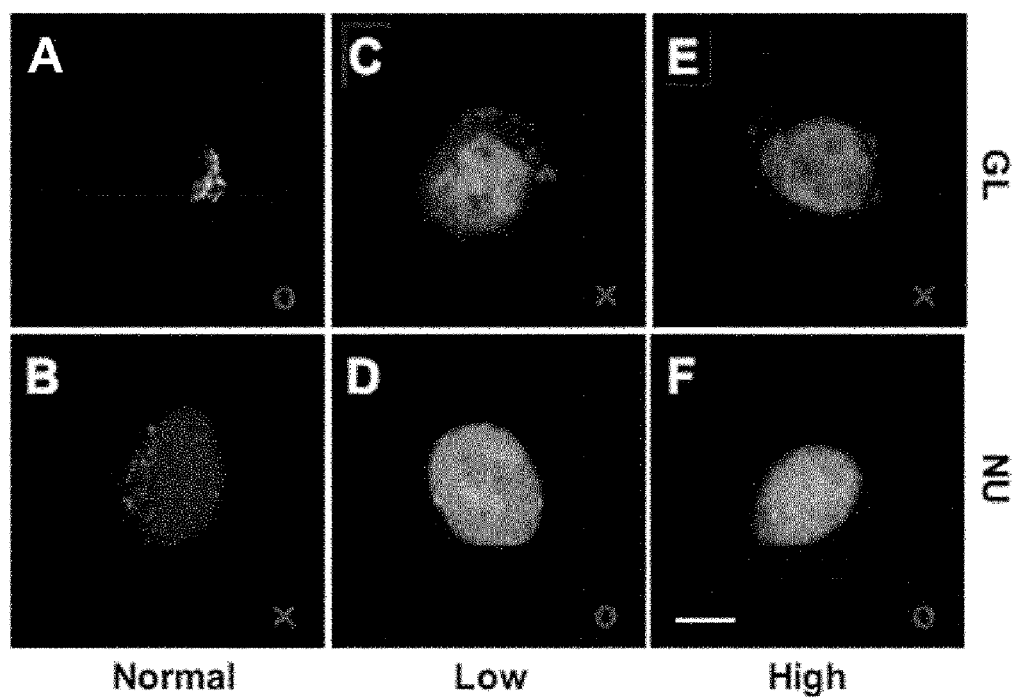
FIG. 8 shows conditional changes in the location of KIF13A. A-F show the confocal images of KIF13A. Markers for the Golgi apparatus (GL, first row) are indicated by red color, and markers for the nucleus (NU, second row) are indicated by blue color under the three conditions of normal, low-grade glioma and high-grade glioma. Yellow (A) and cyan (D and F) represent overlap between KIF13A and the location marker.

Relocation of KIF13A and Changes of Neighboring Proteins Interacting Therewith During Glioma Progression In normal brain, KIF13A (kinesin family member 13A) showed the highest signal in the Golgi apparatus, whereas in low- and high-grade gliomas, it showed the highest signal in the nucleus (FIG. 8). The relocation of KIF13A from the Golgi apparatus to the nucleus during glioma progression was confirmed by in-vivo imaging (FIGS. 8A-8F). The relocation was frequent in a large population of primary glioma cells (>50,000 cells). In glioma cells, approximately 87% of KIF13A overlaps with markers for the nucleus, while in normal cells approximately 13% of KIF13A overlaps with markers for the nucleus. However, the results were reversed in the Golgi apparatus.

Example 14

Relocation of RNF138 and TLX3 During Glioma Progression

Figure 9A:
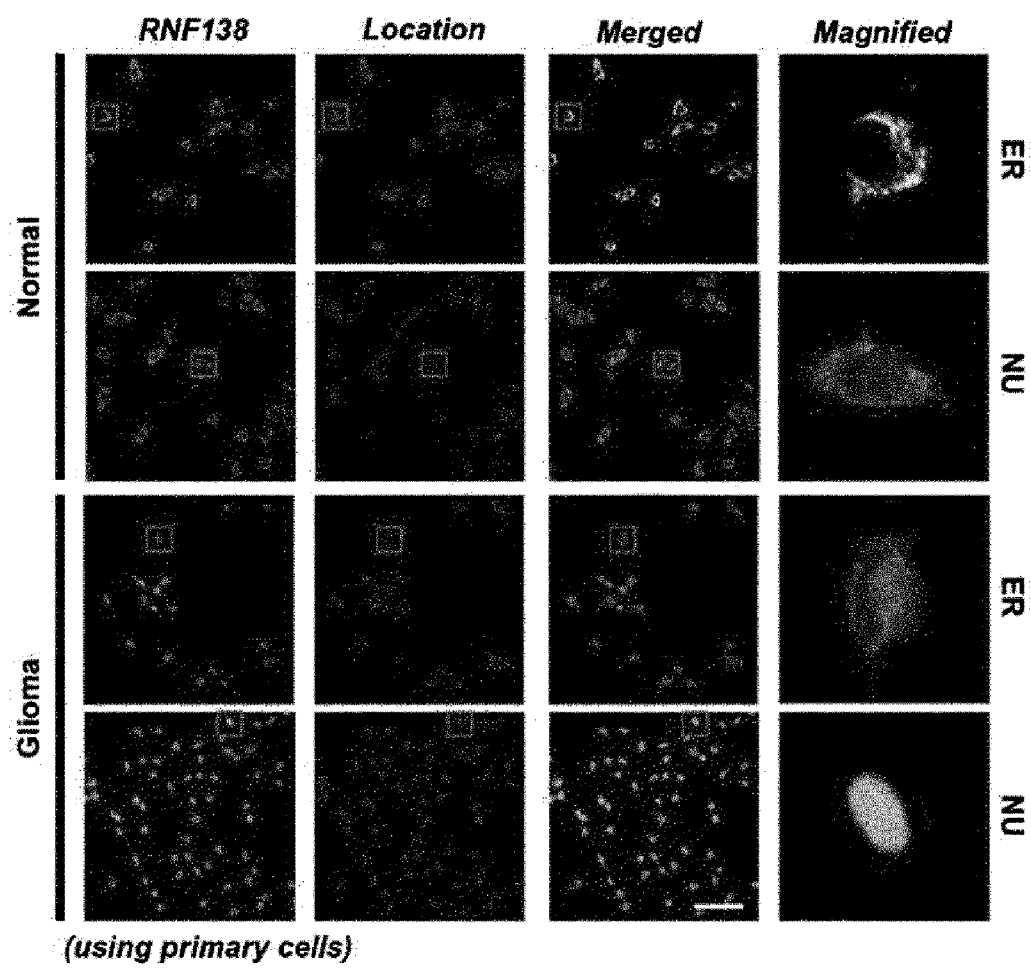
FIG. 9a shows conditional changes in the subcellular location of RNF138. Overlap between RNF138 and the endoplasmic reticulum (ER) marker (red) or the nucleus (NU) marker (blue) was examined in normal cells and glioma cells, and the last column 'Magnified' is for the 14× magnification of the images which are indicated by the red rectangles in the first three columns. Cyan means overlap between each protein and each location marker.

In order to confirm the relocation of RNF138 (E3 ubiquitin ligase) from the endoplasmic reticulum to the nucleus during glioma progression, in vivo imaging confirmed that RNF138 overlaps with markers for the endoplasmic reticulum in normal cells, while it overlaps with markers for the nucleus in glioma cells (FIG. 9a). Cellular subfractionation and Western blotting further confirmed the relocation of RNF138 (FIG. 9b).

Figure 10A:
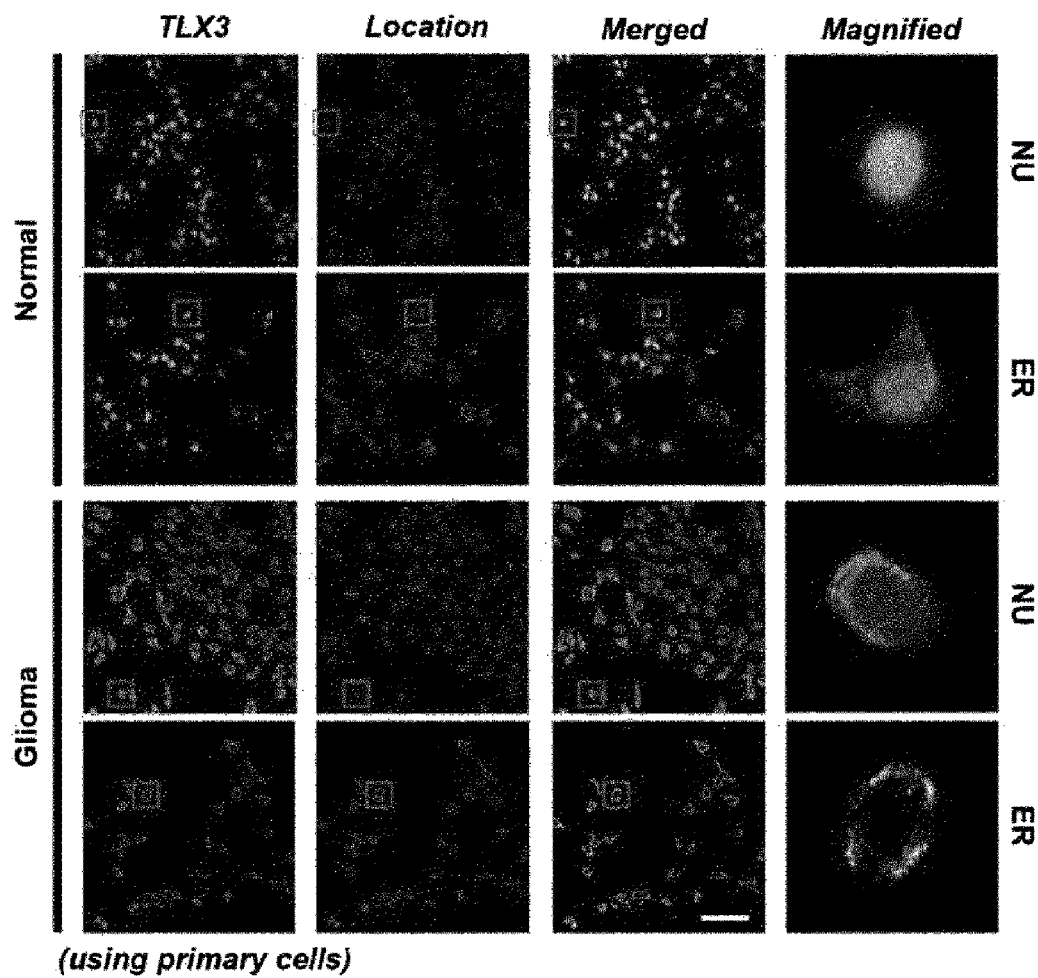
FIG. 10a shows conditional changes in the subcellular location of TLX3. Overlap between TLX3 and the endoplasmic reticulum (ER) marker (red) or the nucleus (NU) marker (blue) was examined in normal cells and glioma cells.
Figure 10B:
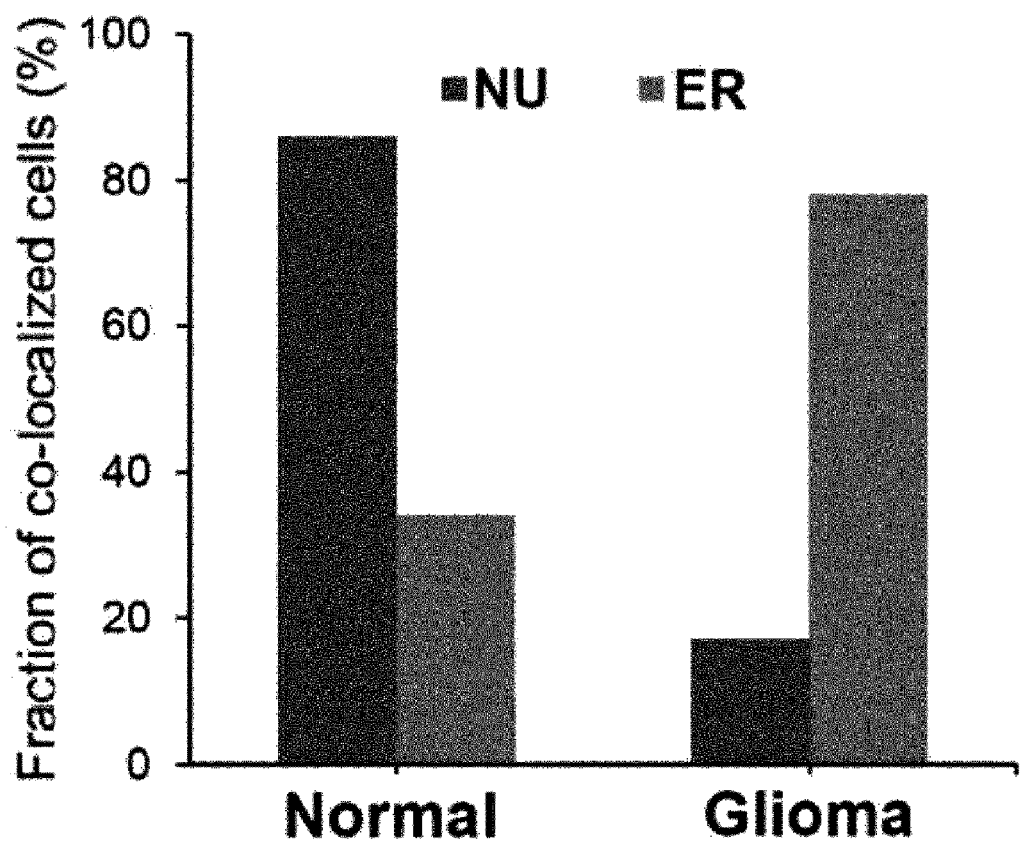
FIG. 10b shows conditional changes in the subcellular location of TLX3. The upper panel shows the percentage of proteins in the endoplasmic reticulum and the nucleus, and the lower panel shows TLX3 locations in normal cells and glioma cells by Western blot.
Figure 10B:
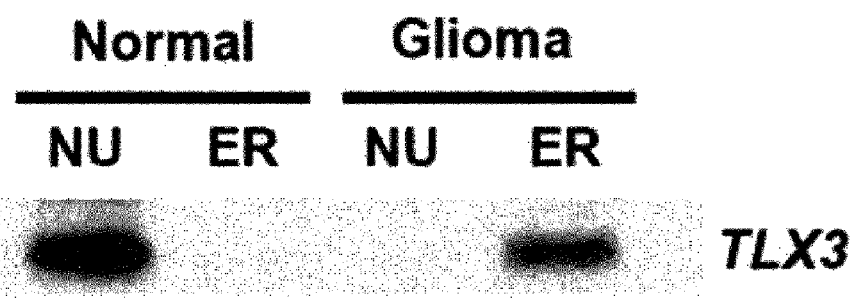
Figure 11A:
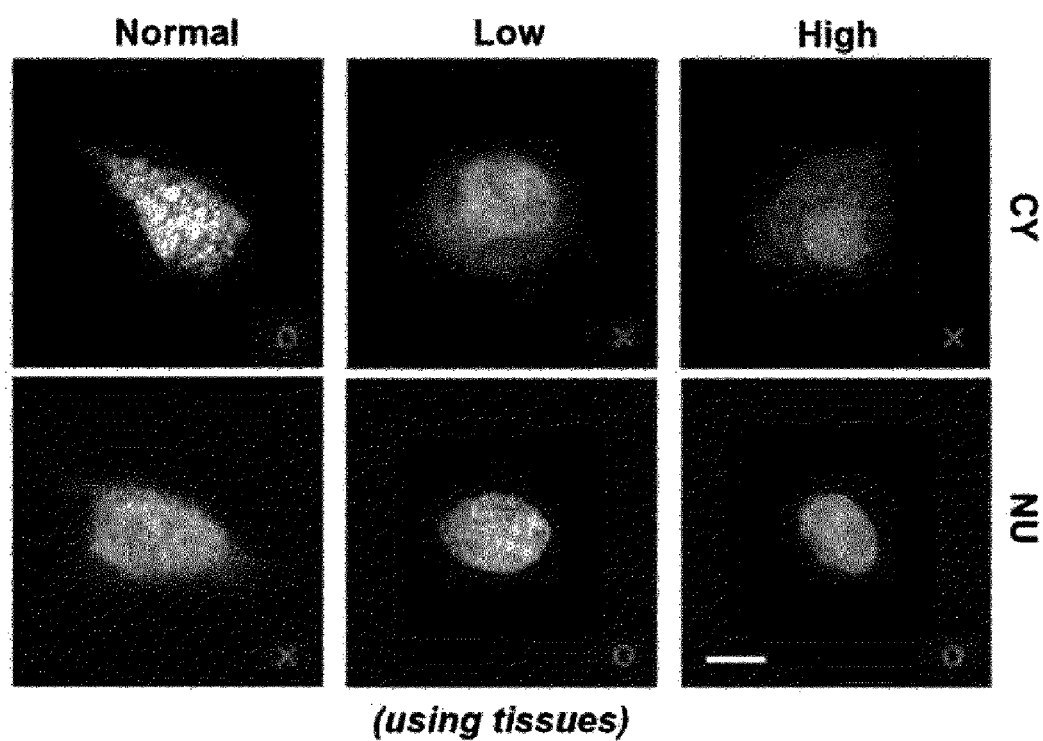
FIG. 11a shows changes in the subcellular location of ATIC during glioma progression. The upper panel shows confocal images for ATIC relocation in normal cells, low-grade glioma cells and high-grade glioma cells. ATIC relocated from the cytosol (CY) to the nucleus (NU) with glioma progression.
Figure 11B:
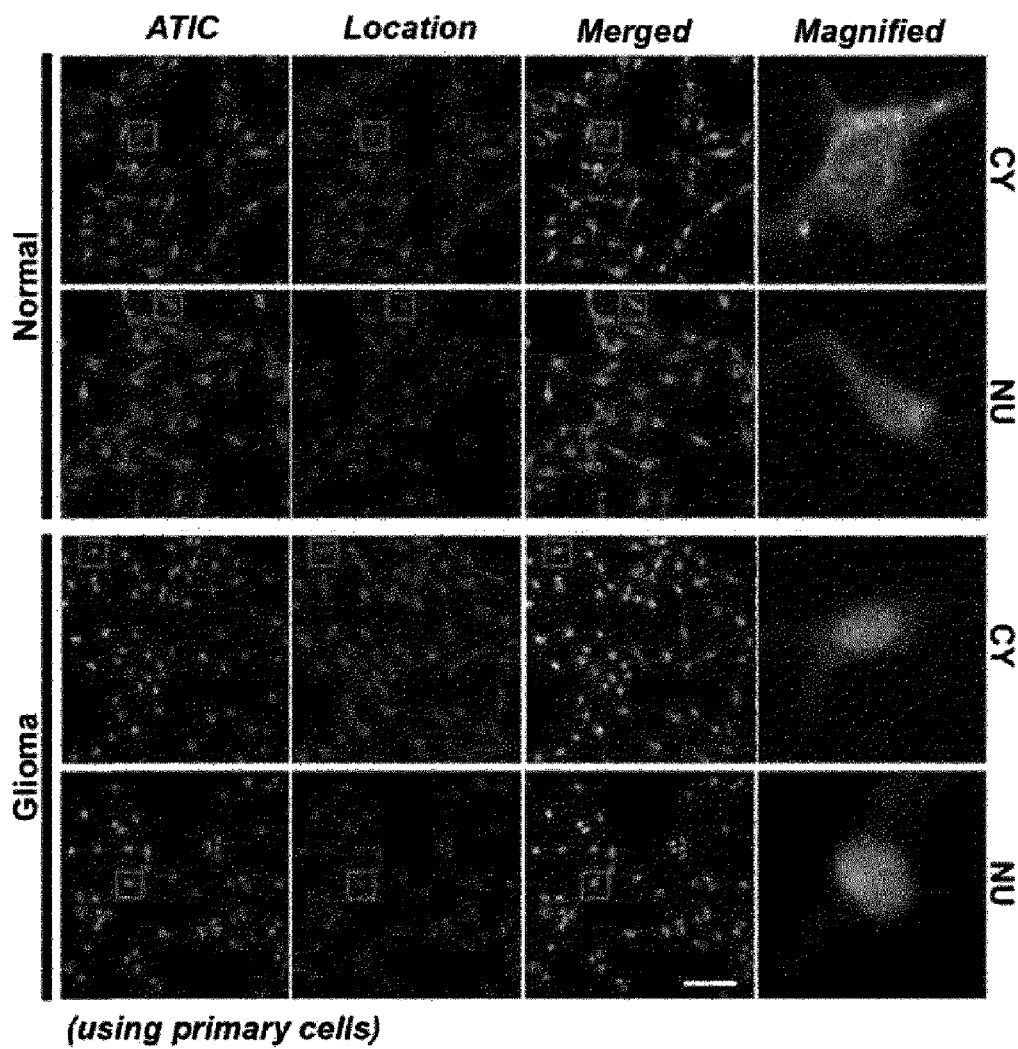
FIG. 11b shows conditional changes in the subcellular location of ATIC. Overlap between ATIC and the cytosol marker or the nucleus marker was examined in normal cells and glioma cells.
Figure 11C:
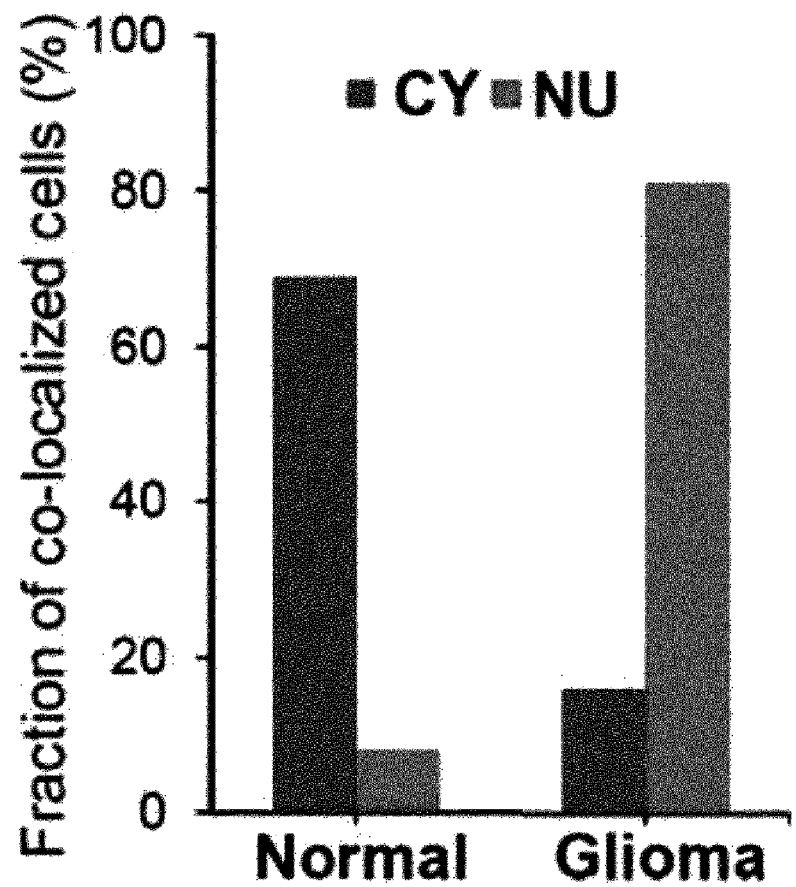
FIG. 11c snows conditional changes in the subcellular location of ATIC. The upper panel snows the percentage of proteins in the cytosol and the nucleus, and the lower panel shows ATIC locations in normal cells and glioma cells by Western blot.
Figure 11C:
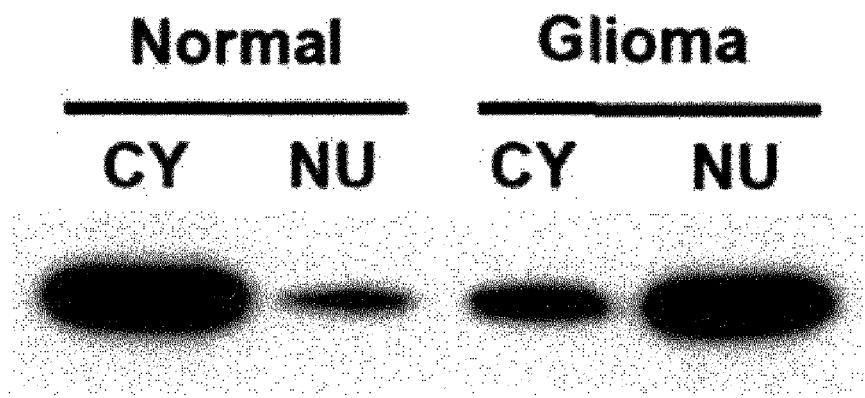

Further, relocation of TLX3 (T-cell leukemia homeobox 3), which is a member of a family of orphan homeobox genes encoding DNA-binding nuclear transcription factors, from the nucleus to the endoplasmic reticulum was also observed during glioma progression (FIG. 10).

Example 15

Relocation Proteins During Glioma Progression

Figure 12A:
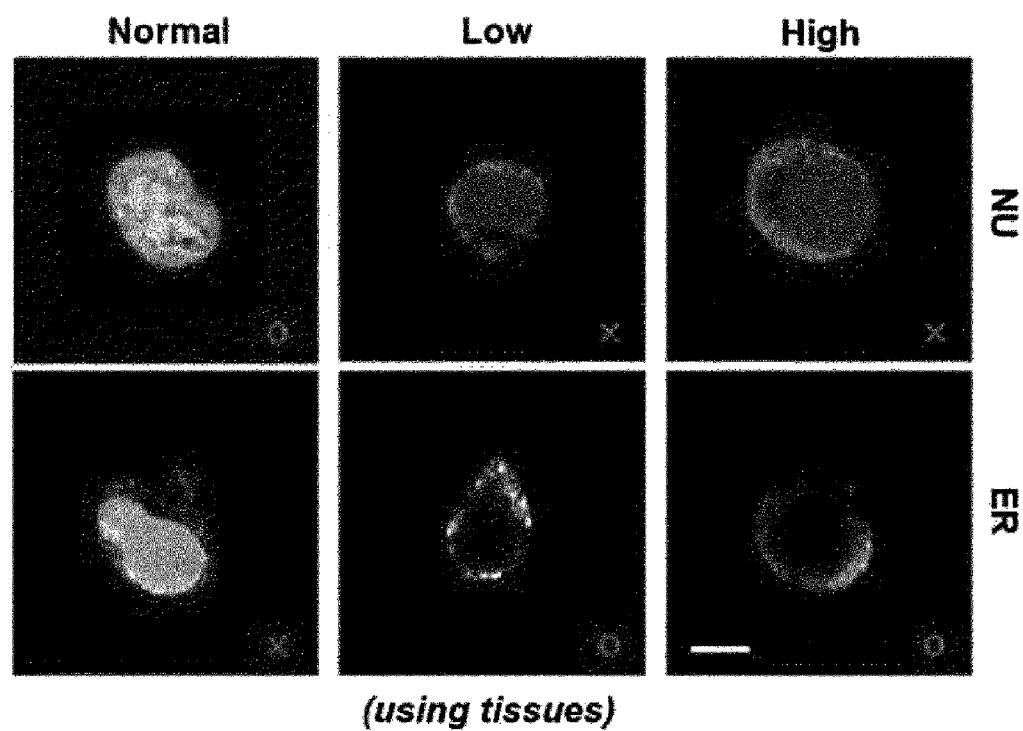
FIG. 12a shows changes in the subcellular location of DIP2A during glioma progression, and shows confocal images for DIP2A relocation in normal cells, low-grade glioma cells and high-grade glioma cells. DIP2A relocated from the nucleus (NU) to the endoplasmic reticulum (ER) with glioma progression.
Figure 12C:
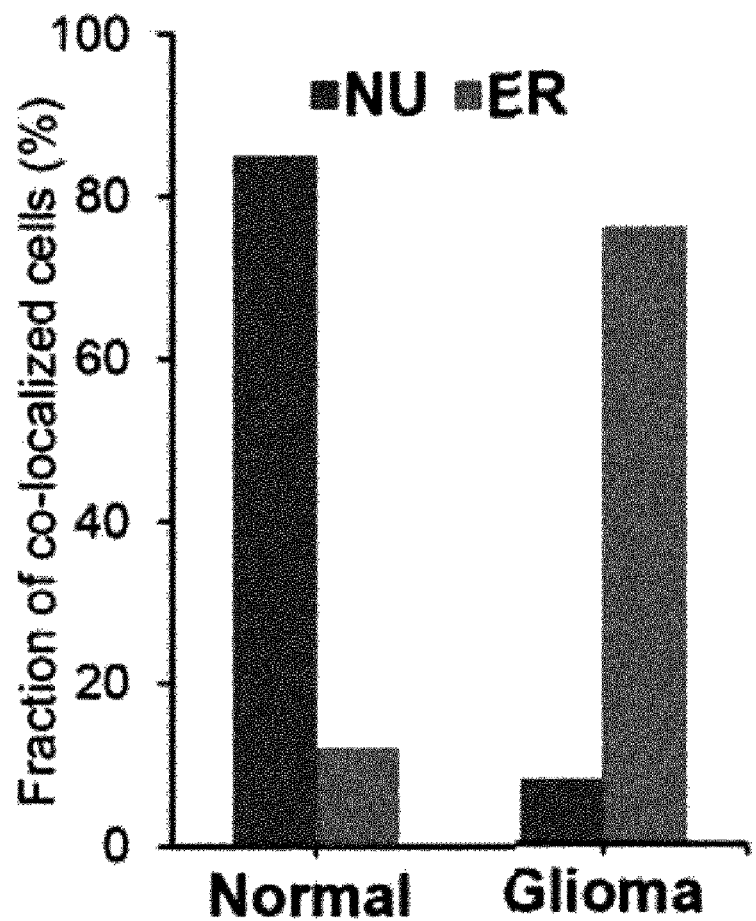
FIG. 12c shows conditional changes in the subcellular location of DIP2A. The upper panel shows the percentage of proteins in the nucleus and the endoplasmic reticulum, and the lower panel shows DIP2A locations in normal cells and glioma cells by Western blot.
Figure 12C:
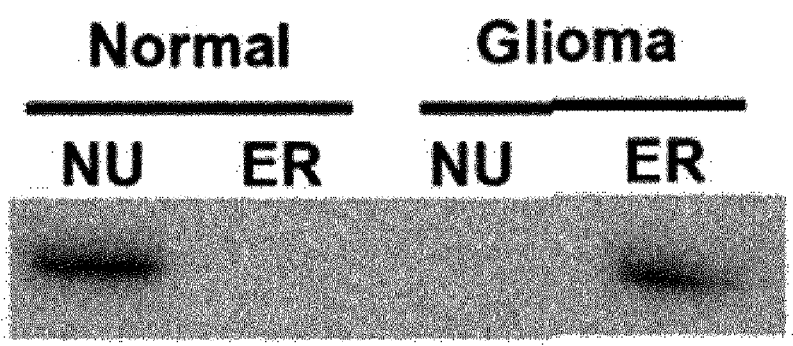
Figure 13A:
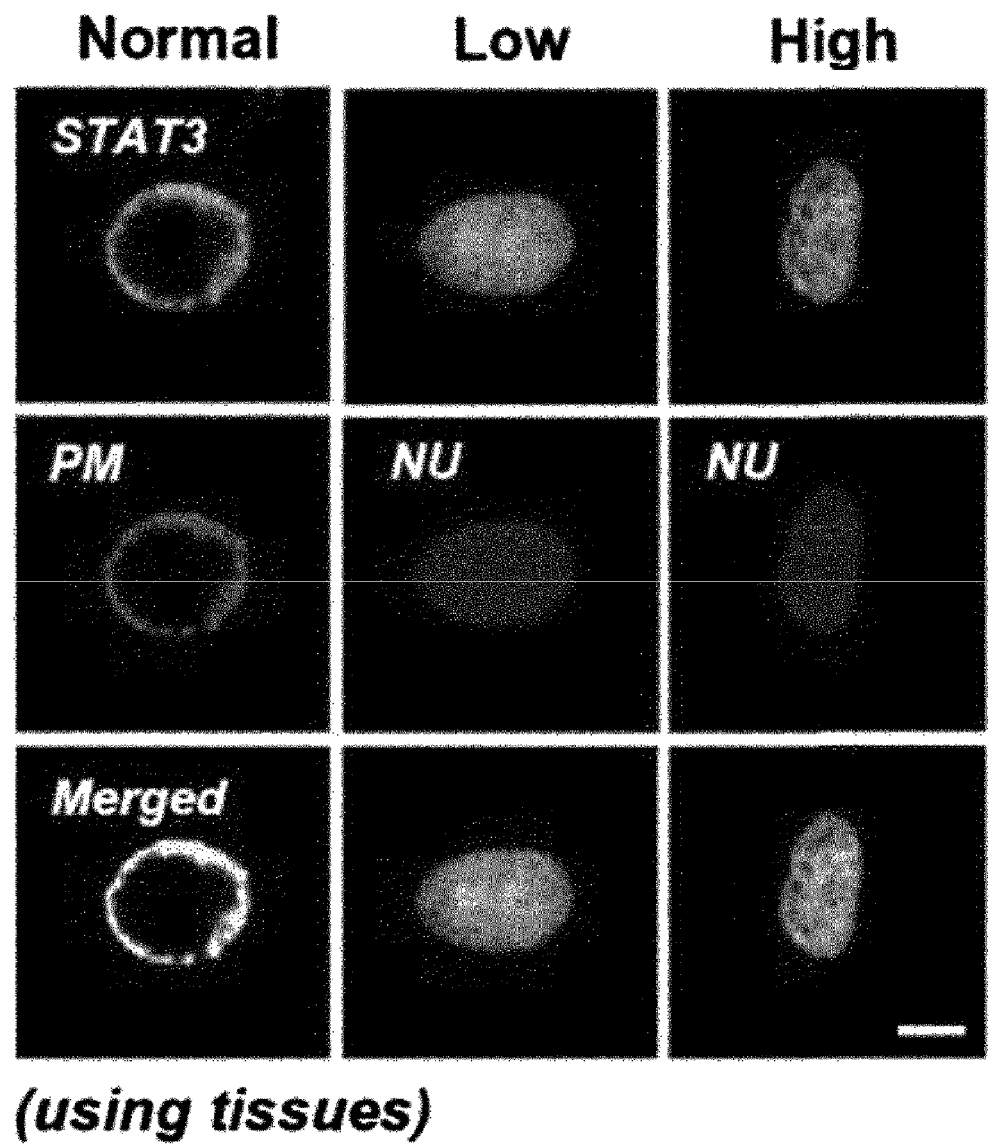
FIG. 13a shows changes in the subcellular location of STAT3 during glioma progression, and shows confocal images for STAT3 relocation in normal cells, low-grade glioma cells and high-grade glioma cells. STAT3 relocated from the plasma membrane (PM) to the nucleus (NU) with glioma progression.
Figure 13B:
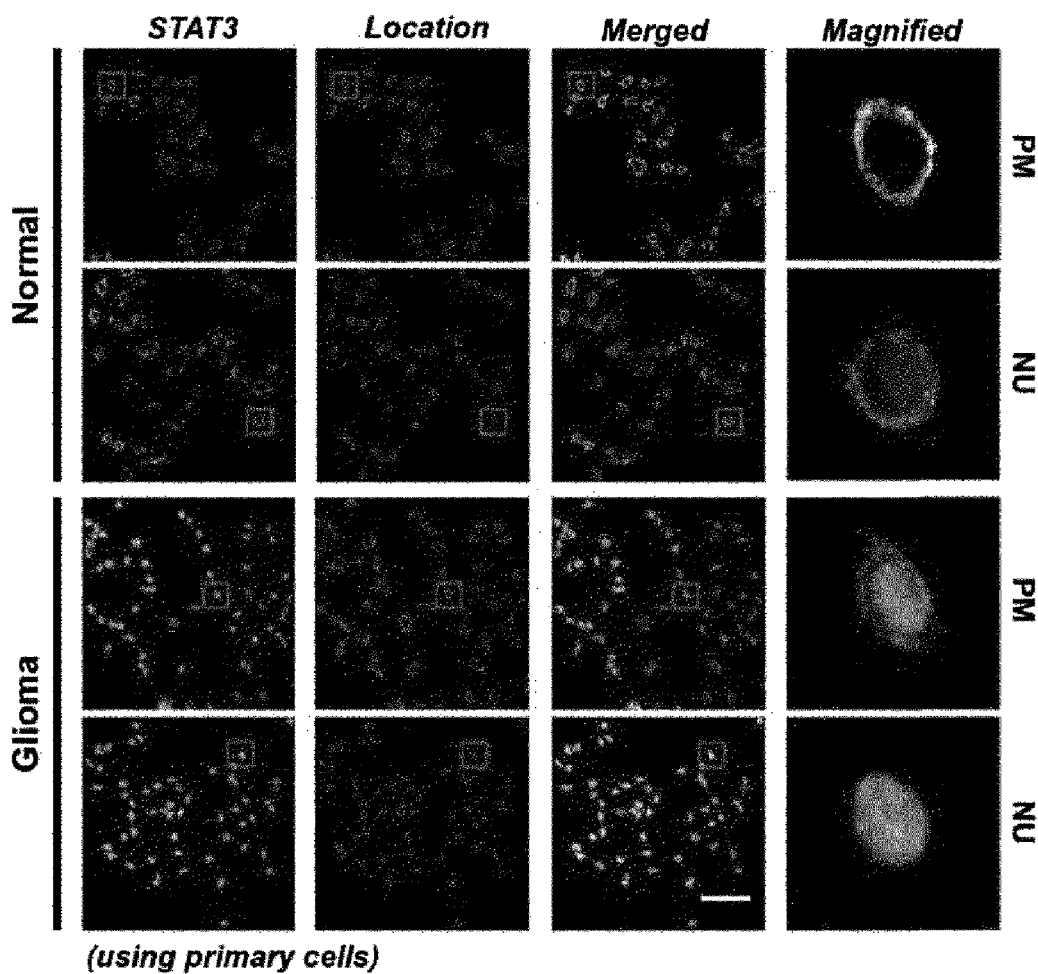
FIG. 13b snows conditional changes in the subcellular location of STAT3. Overlap between STAT3 and the plasma membrane marker or the nucleus marker was examined in normal cells and glioma cells.
Figure 13C:
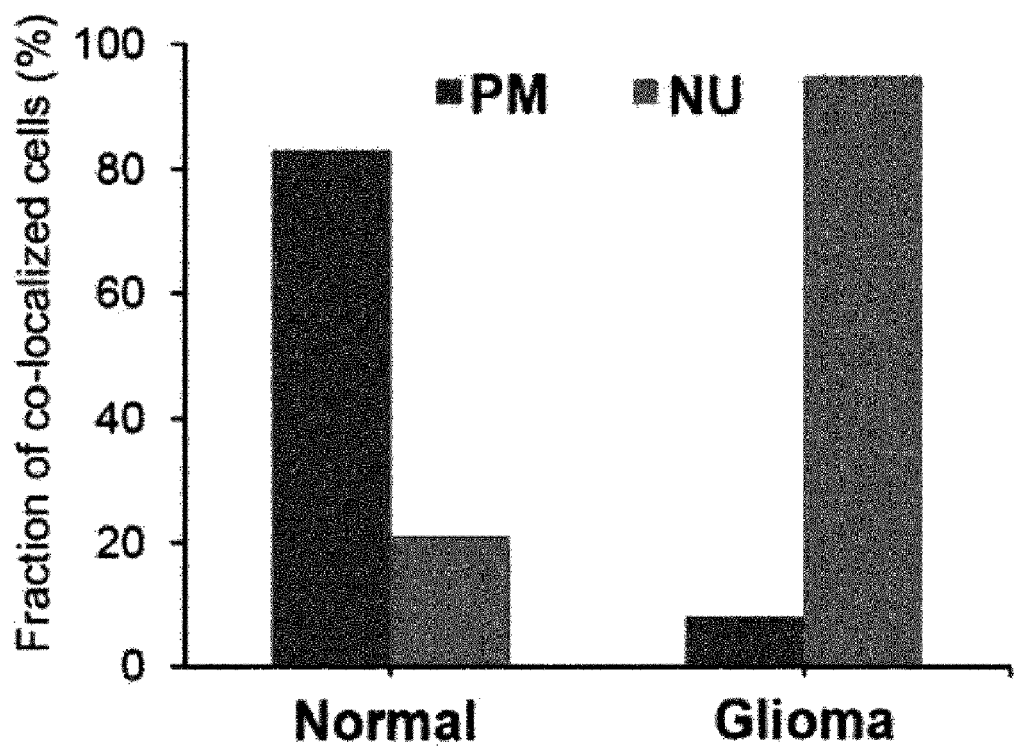
FIG. 13c shows conditional changes in the subcellular location of STAT3. The upper panel shows the percentage of proteins in the plasma membrane and the nucleus, and lower panel shows STAT3 locations in normal cells and glioma cells by Western blot.
Figure 13C:
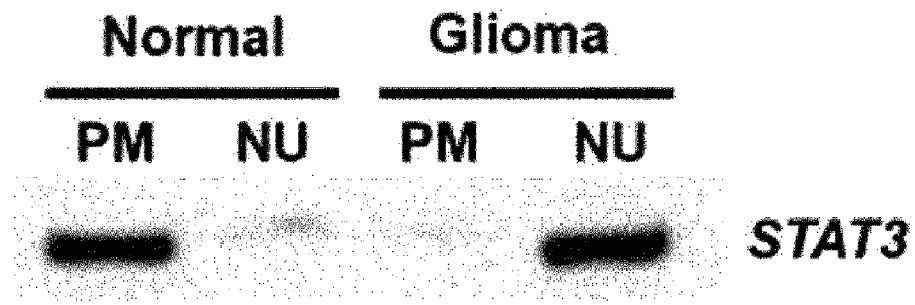
Figure 14C:
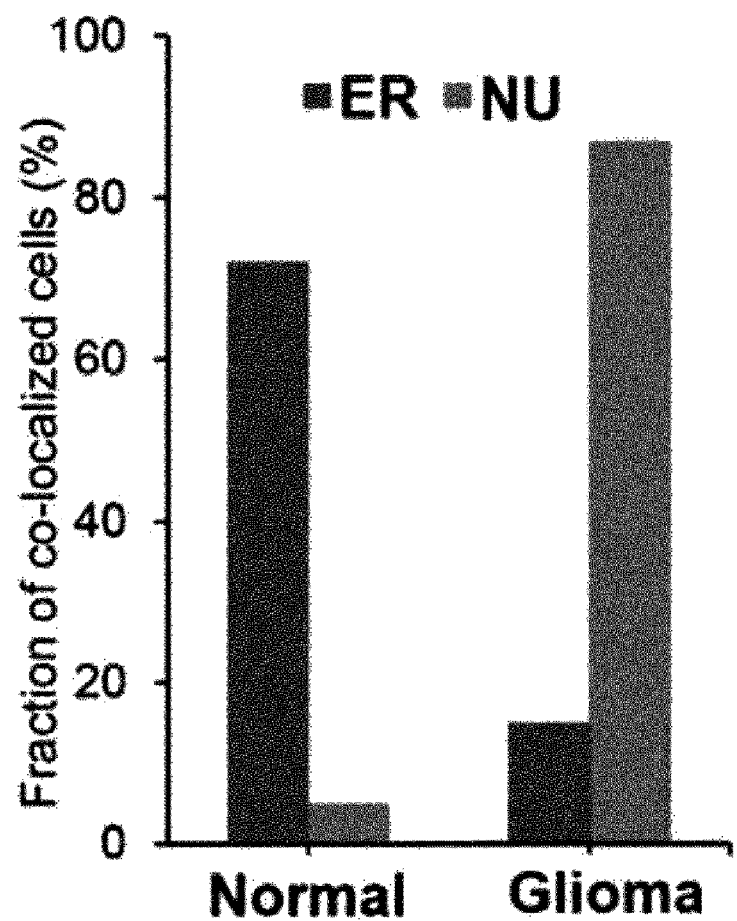
FIG. 14c shows conditional changes in the subcellular location of DLX2. The upper panel shows the percentage of proteins in the endoplasmic reticulum and the nucleus, and the lower panel shows DLX2 locations in normal cells and glioma cells by Western blot.
Figure 14C:
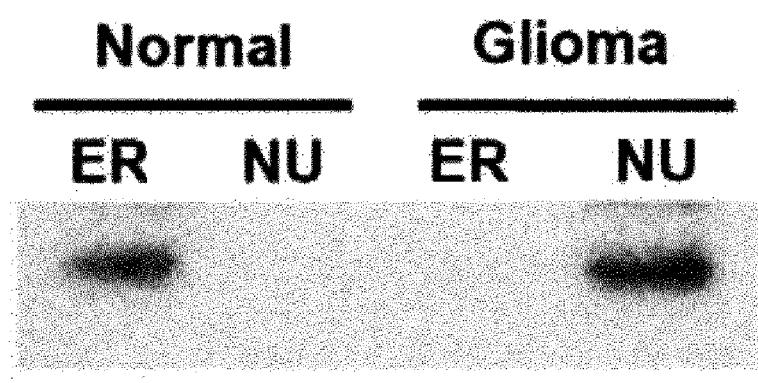
Figure 15A:
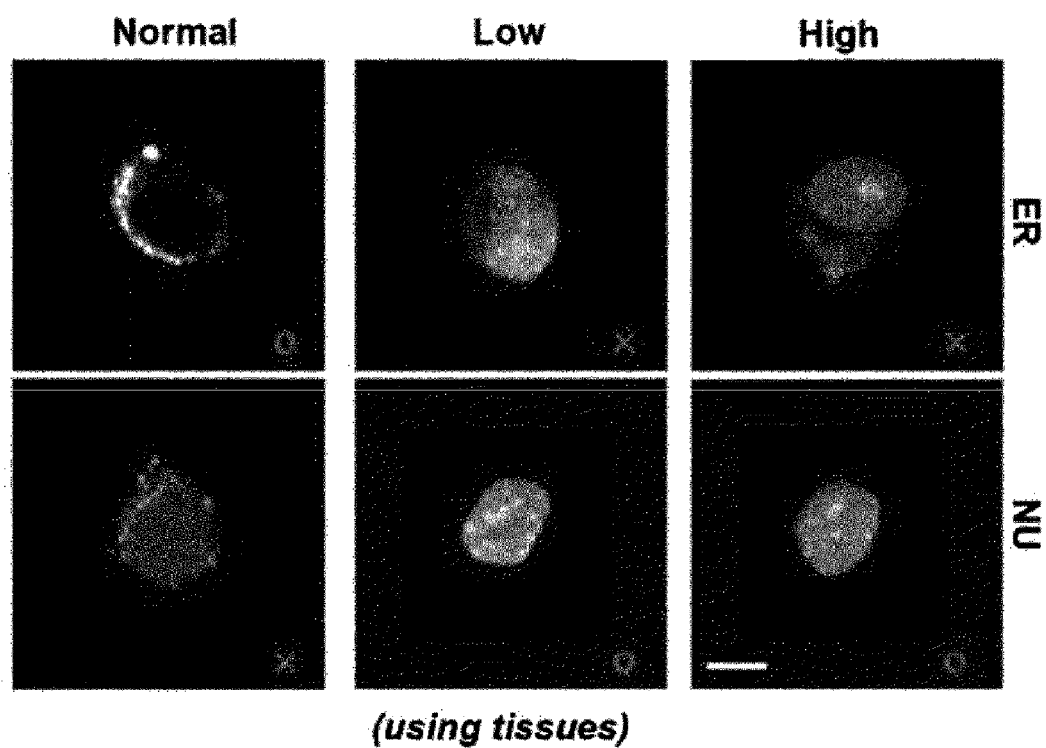
FIG. 15a shows changes in the subcellular location of TBX19 during glioma progression, and shows confocal images for TBX19 relocation in normal cells, low-grade glioma cells and high-grade glioma cells. TBX19 relocated from the endoplasmic reticulum (ER) to the nucleus (NU) with glioma progression.
Figure 15C:
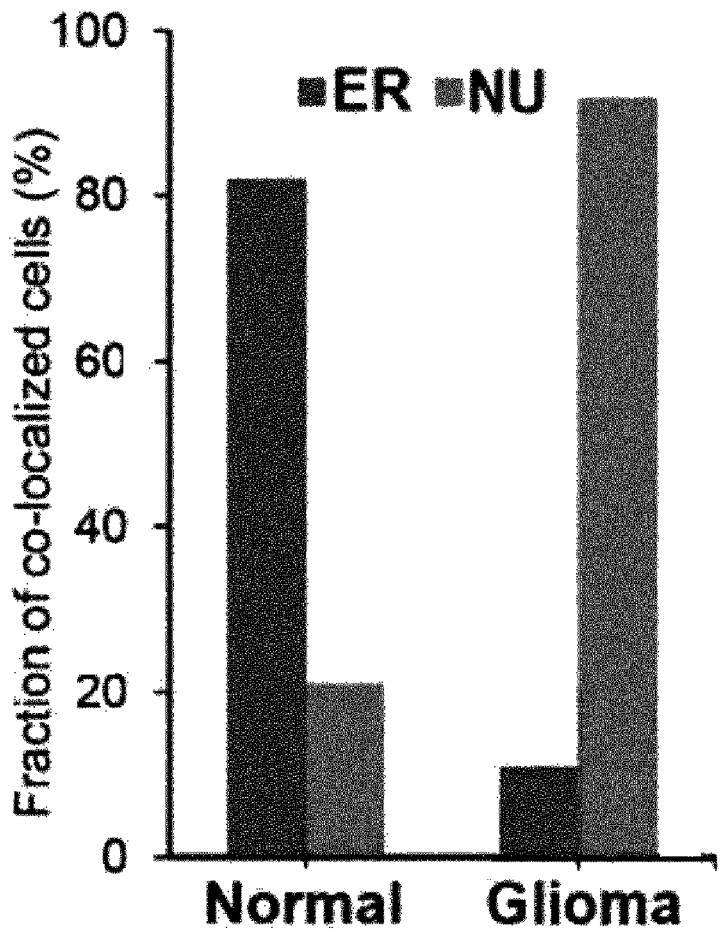
FIG. 15c snows conditional changes in the subcellular location of TBX19. Upper panel shows the percentage of proteins in the endoplasmic reticulum and the nucleus, and lower panel shows TBX19 locations in normal cells and glioma cells by Western blot.
Figure 15C:
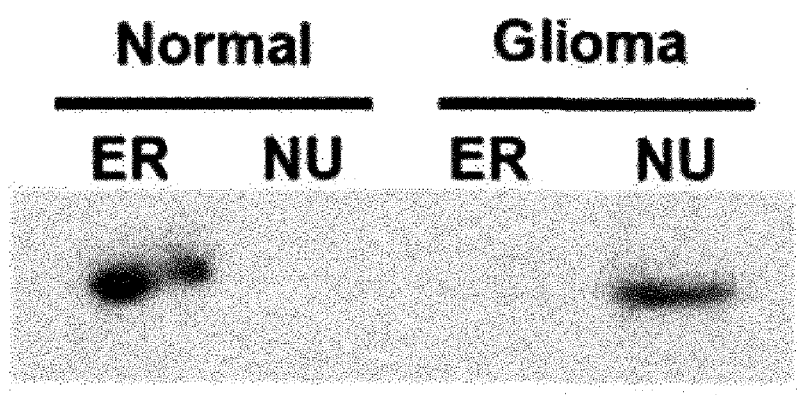
Figure 16A:
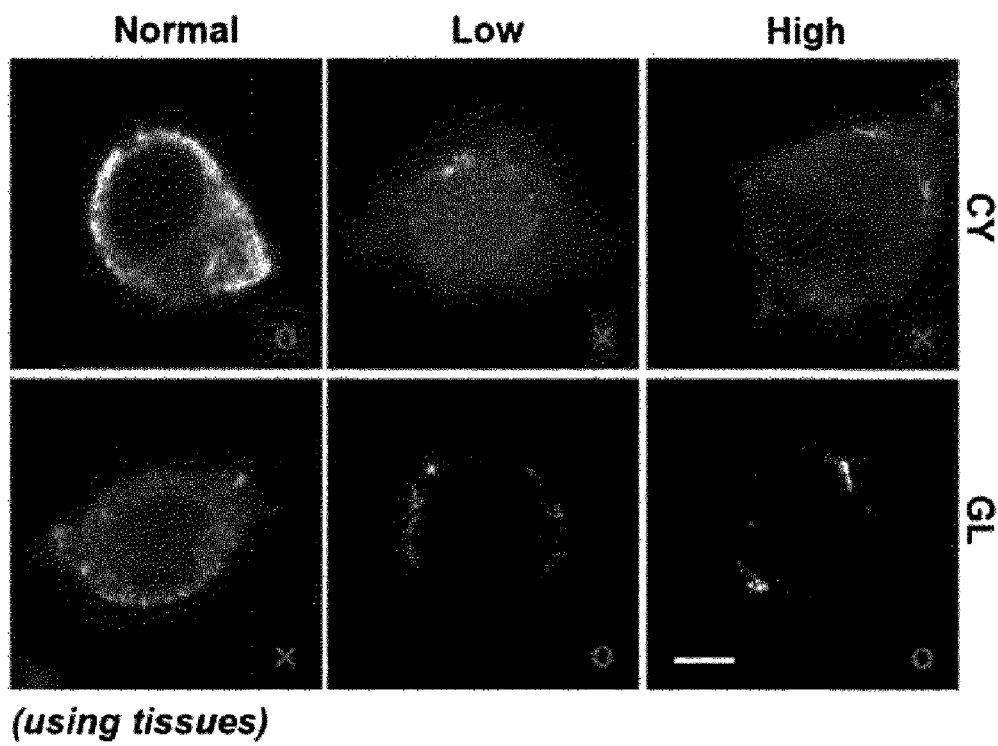
FIG. 16a shows changes in the subcellular location of AGAP1 during glioma progression. The upper panel shows confocal images for AGAP1 relocation in normal cells, low-grade glioma cells and high-grade glioma cells, in which AGAP1 relocated from the cytosol (CY) to the Golgi apparatus (GL) with glioma progression. The lower panel shows the percentage of proteins in the cytosol and the Golgi apparatus.
Figure 16A:
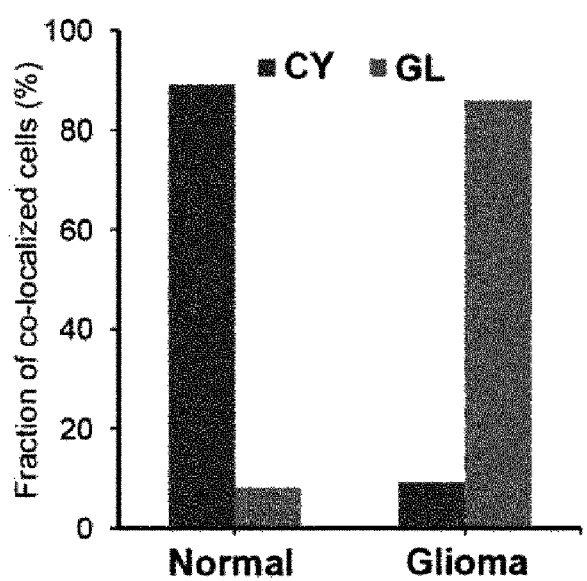
Figure 16B:
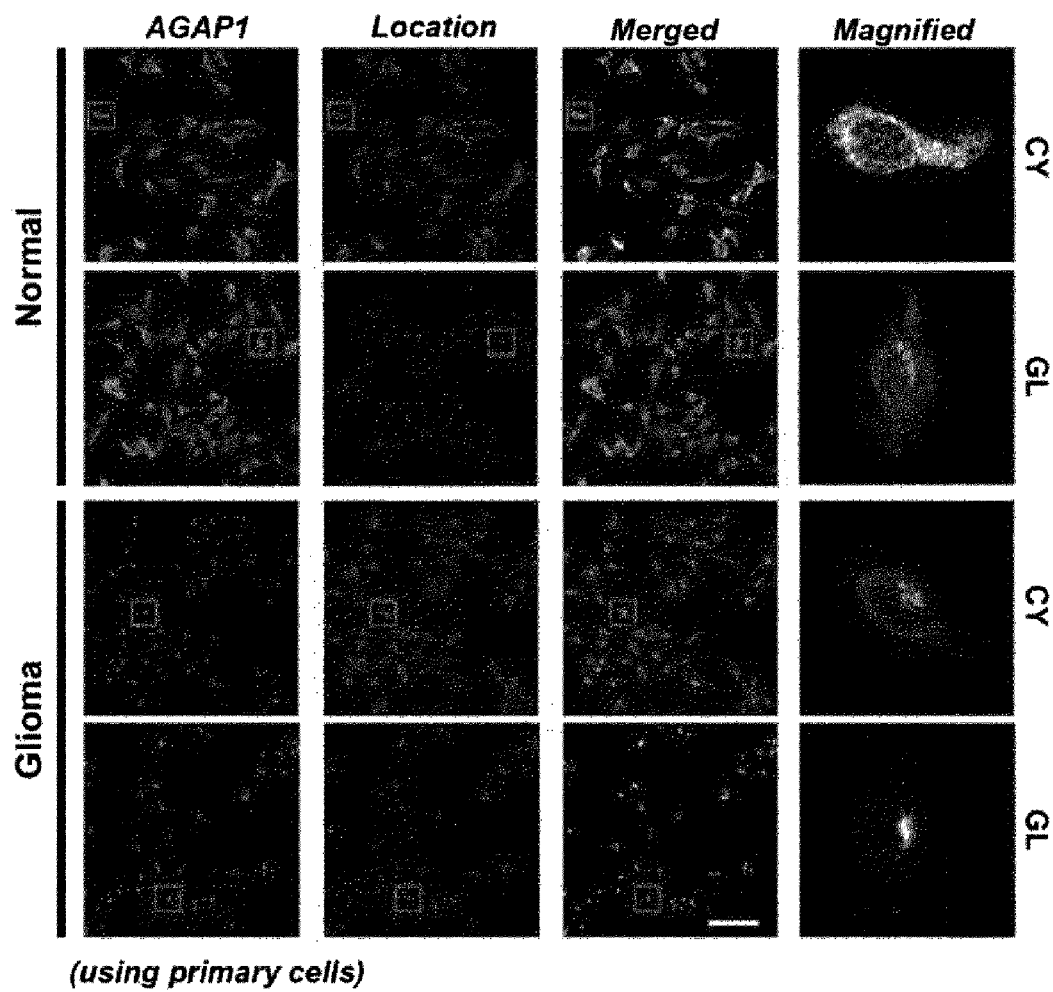
FIG. 16b shows conditional changes in the subcellular location of AGAP1. Overlap between AGAP1 and the cytosol marker or the Golgi apparatus marker was examined in normal cells and glioma cells.
Figure 17A:
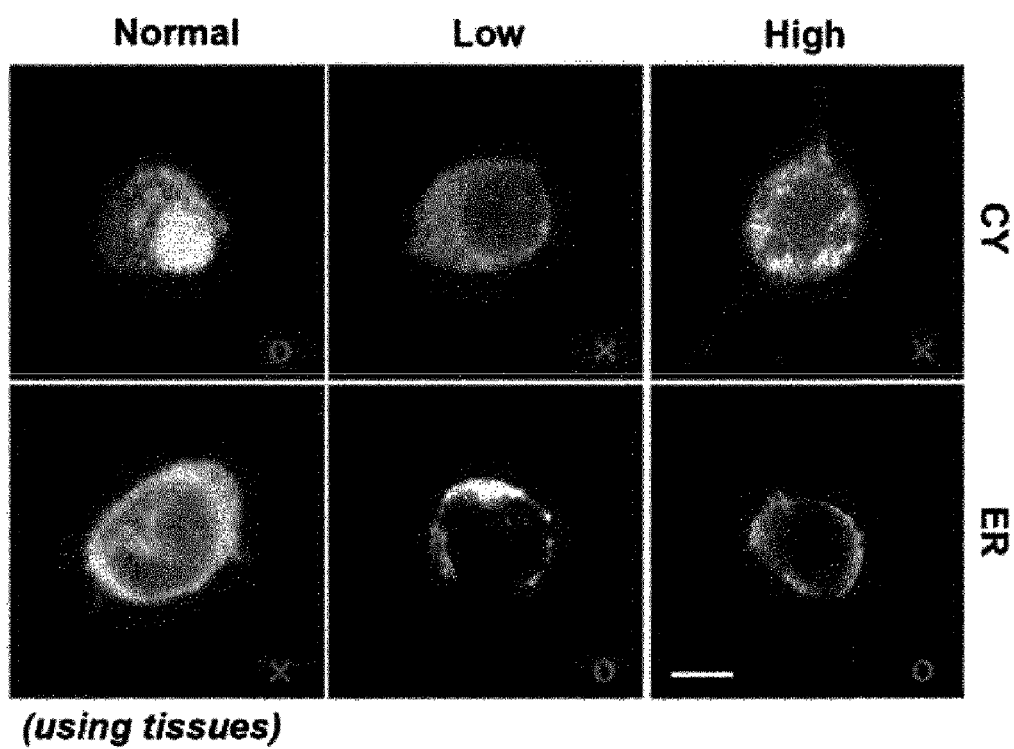
FIG. 17a shows changes in the subcellular location of CPB1 during glioma progression, and shows confocal images for CPB1 relocation in normal cells, low-grade glioma cells and high-grade glioma cells. CPB1 relocated from the cytosol (CY) to the endoplasmic reticulum (ER) with glioma progression.
Figure 17C:
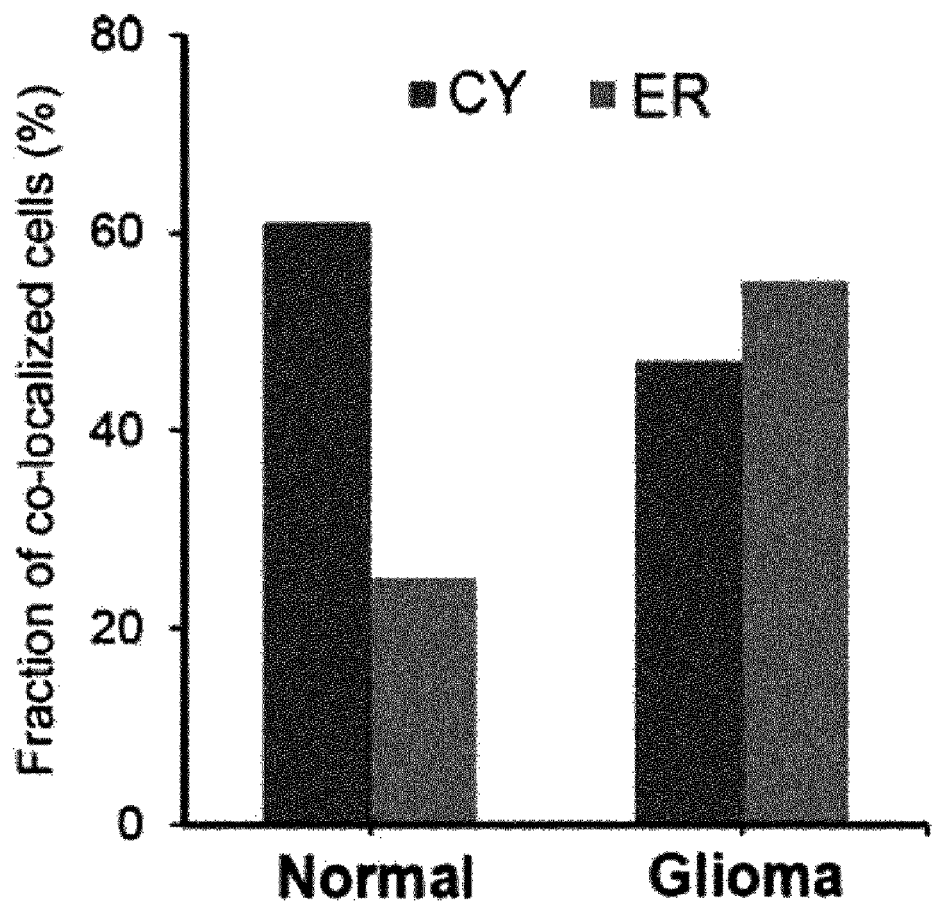
FIG. 17c shows conditional changes in the subcellular location of CPB1. The upper panel shows the percentage of proteins in the cytosol and the endoplasmic reticulum, and the lower panel shows CPB1 locations in normal cells and glioma cells by Western blot.
Figure 17C:
Figure 18A:
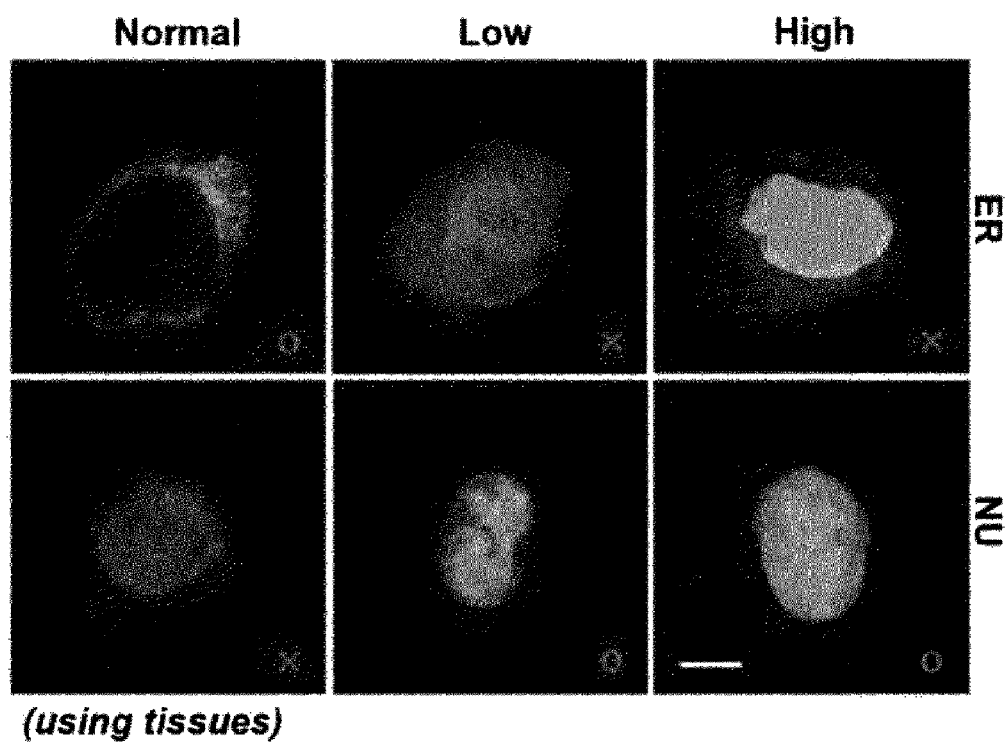
FIG. 18a shows changes in the subcellular location of NFRκB during glioma progression, and shows confocal images for NFRκB relocation in normal cells, low-grade glioma cells and high-grade glioma cells. NFRκB relocated from the endoplasmic reticulum (ER) to the nucleus (NU) with glioma progression.
Figure 18B:
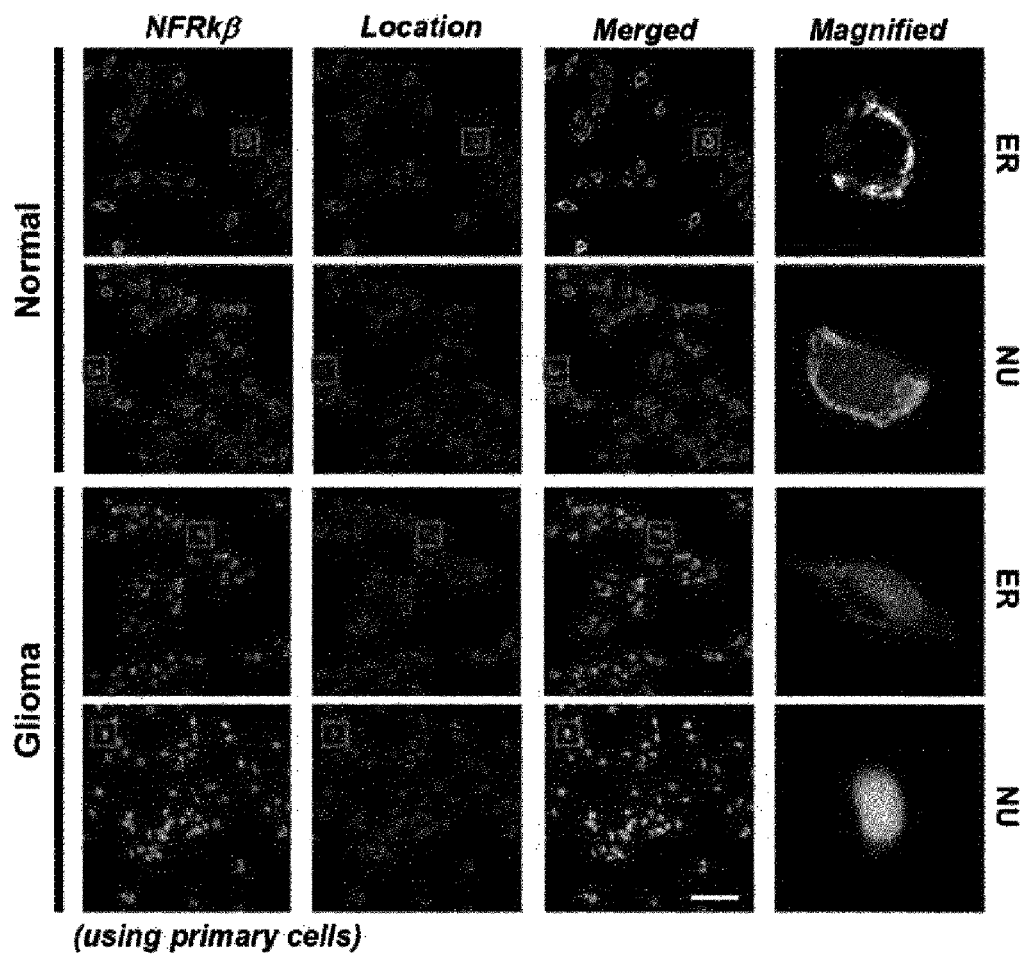
FIG. 18b shows conditional changes in the subcellular location of NFRκB. Overlap between NFRκB and the endoplasmic reticulum marker or the nucleus marker was examined in normal cells and glioma cells.
Figure 18C:
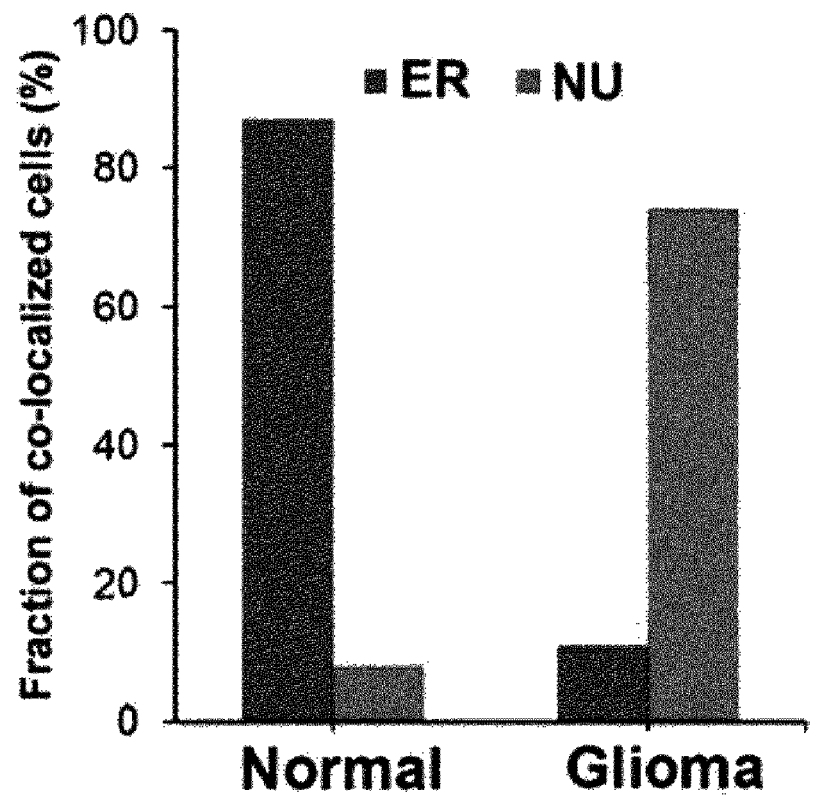
FIG. 18c shows conditional changes in the subcellular location of NFRκB. The upper panel shows the percentage of proteins in the endoplasmic reticulum and the nucleus, and the lower panel shows NFRκB locations in normal cells and glioma cells by Western blot.
Figure 18C:
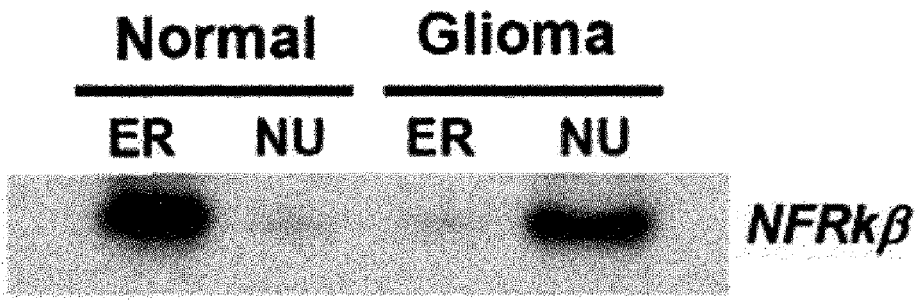
Figure 19C:
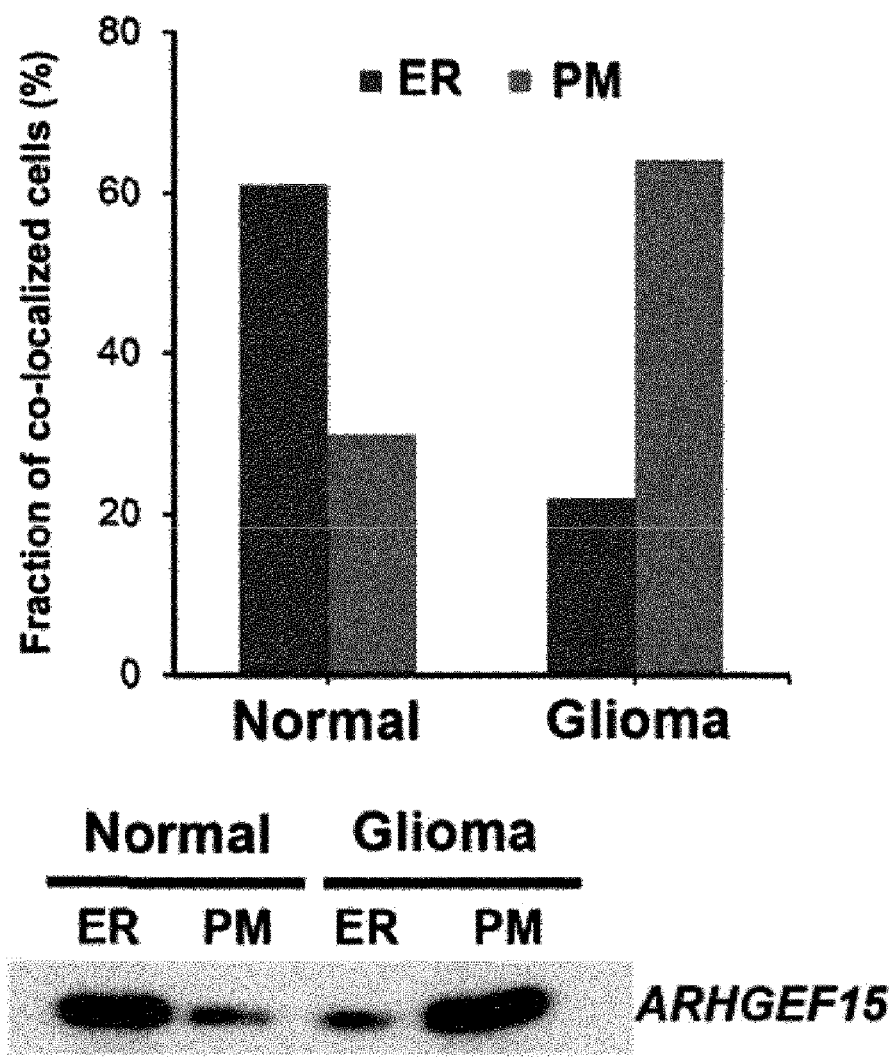
FIG. 19c shows conditional changes in the subcellular location or ARHGEF15. The upper panel shows the percentage of proteins in the endoplasmic reticulum and the plasma membrane, and the lower panel shows ARHGEF15 locations in normal cells and glioma cells by Western blot.
Figure 20A:
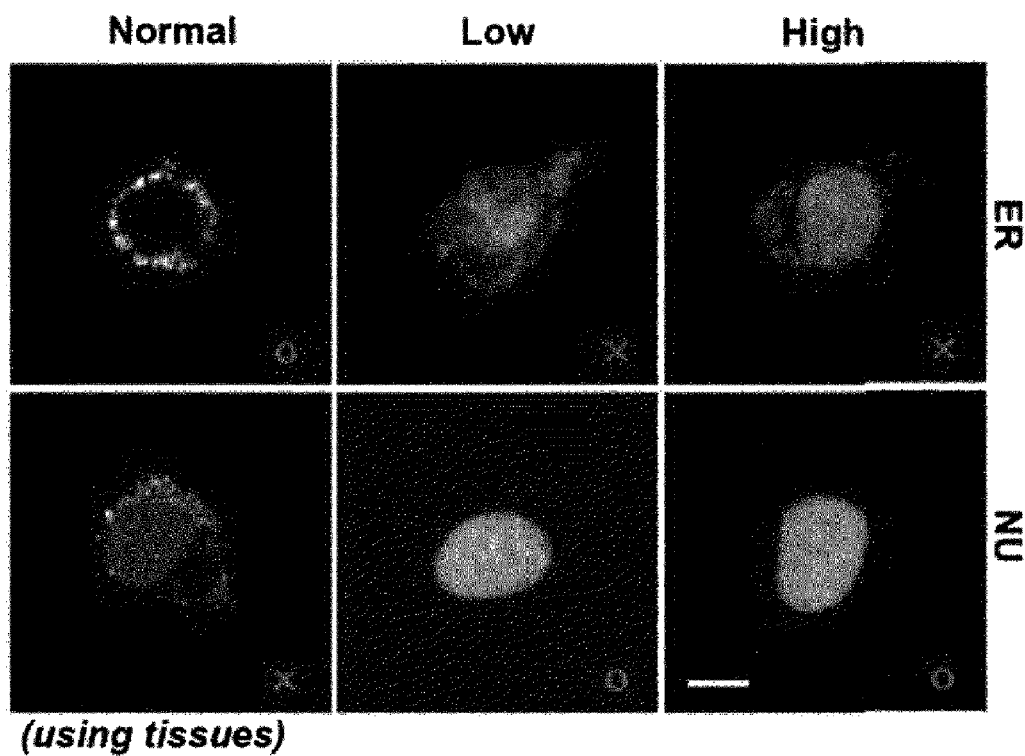
FIG. 20a shows changes in the subcellular location of CLK2 during glioma progression, and shows confocal images for CLK2 relocation in normal cells, low-grade glioma cells and high-grade glioma cells. CLK2 relocated from the endoplasmic reticulum (ER) to the nucleus (NU) with glioma progression.
Figure 21A:
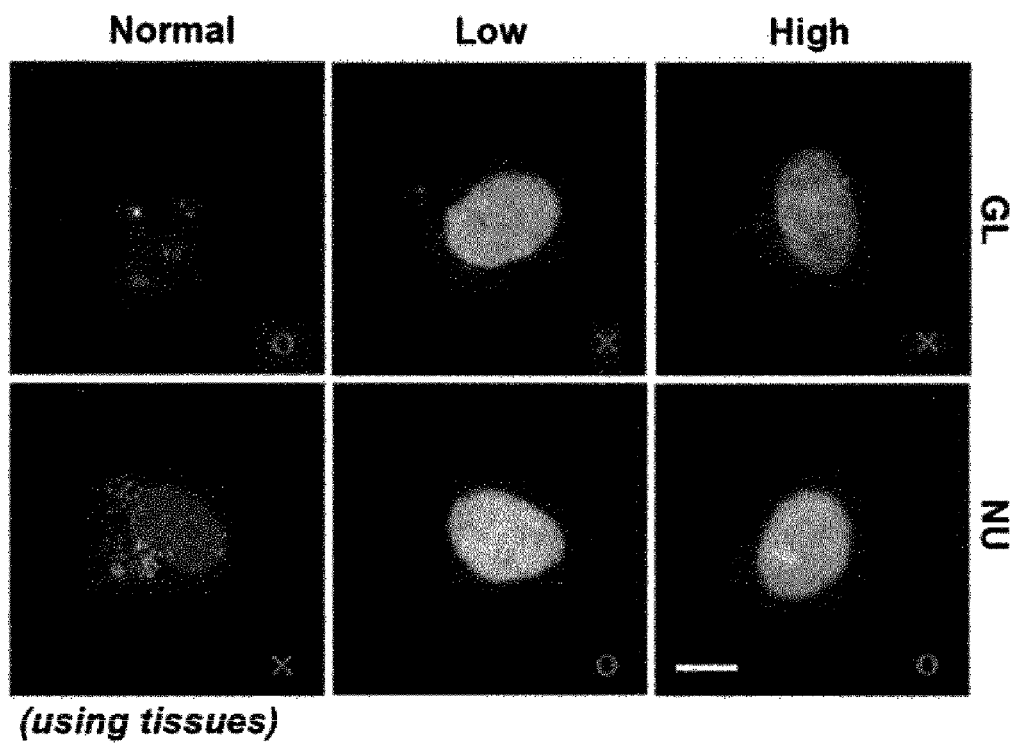
FIG. 21a shows changes in the subcellular location of SYT9 during glioma progression. The upper panel shows confocal images for SYT9 relocation in normal cells, low-grade glioma cells and high-grade glioma cells, in which SYT9 relocated from the Golgi apparatus (GL) to the nucleus (NU) with glioma progression. The lower panel shows the percentage of proteins in the Golgi apparatus and the nucleus.
Figure 21A:
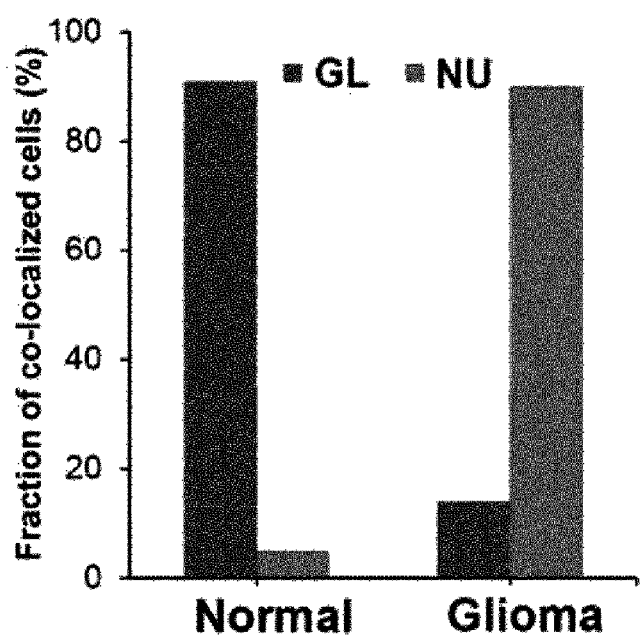

Locations of ATIC (5-aminoimidazole-4-carboxamide ribonucleotide formyltransferase/IMP cyclohydrolase), DIP2A (DIP2 disco-interacting protein 2 homolog A), STAT3 (signal transducer and activator of transcription 3), DLX2 (distal-less homeobox 2), TBX19 (T-box 19), AGAP1 (Arf-GAP with GTPase domain, ankyrin repeat and PH domain 1), CPB1 (carboxypeptidase B1), NFRκB (nuclear factor related to kappaB binding protein), ARHGEF15 (Rho guanine nucleotide exchange factor 15), CLK2 (CDC-like kinase 2) and SYT9 (synaptotagmin IX) proteins differed between normal cells and glioma cells. Specifically, during glioma progression, relocation of ATIC from the cytosol (CY) to the nucleus (NU) (FIG. 11), relocation of DIP2A from the nucleus (NU) to the endoplasmic reticulum (ER) (FIG. 12), relocation of STAT3 from the plasma membrane (PM) to the nucleus (NU) (FIG. 13), relocation of DLX2 from the endoplasmic reticulum (ER) to the nucleus (NU) (FIG. 14), relocation of TBX19 from the endoplasmic reticulum (ER) to the nucleus (NU) (FIG. 15), relocation of AGAP1 from the cytosol (CY) to the Golgi apparatus (GL) (FIG. 16), relocation of CPB1 from the cytosol (CY) to the endoplasmic reticulum (ER) (FIG. 17), relocation of NFRκB from the endoplasmic reticulum (ER) to the nucleus (NU) (FIG. 18), relocation of ARHGEF15 from the endoplasmic reticulum (ER) to the plasma membrane (PM) (FIG. 19), relocation of CLK2 from the endoplasmic reticulum (ER) to the nucleus (NU) (FIG. 20), and relocation of SYT9 from the Golgi apparatus (GL) to the nucleus (NU) (FIG. 21) were observed.

Example 16

Effect of GFRα4 Relocation on Glioma Prognosis

In the present invention, a correlation between GFRα4 location in patients after glioma surgery and prediction of prognosis after glioma surgery was examined.

Figure 22:
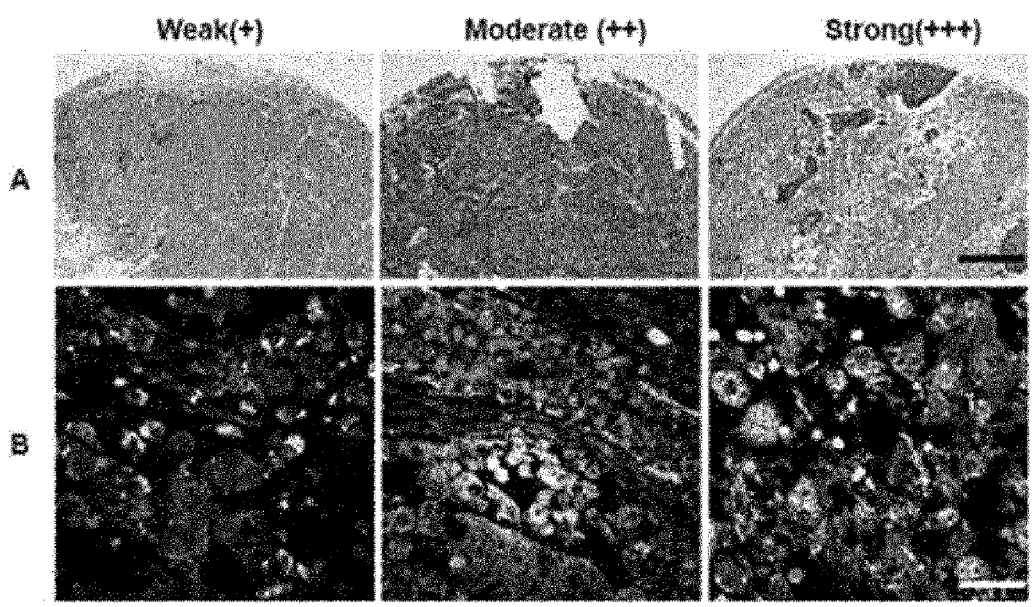
FIG. 22 shows that prognosis after glioma surgery is poorer, as GFRα4 relocates to the endoplasmic reticulum.

Postoperative prognosis was examined by eosin staining of the tissue of a patient after glioma surgery. Prognosis was graded according to the intensity of eosin staining: weak (+), moderate (++), and strong (+++) (FIG. 22A). In the present invention, fluorescence imaging showed GFRα4 relocation from the plasma membrane to the endoplasmic reticulum in the tissue of the patient after glioma surgery, and as prognosis after glioma surgery was poorer, GFRα4 relocated from the plasma membrane to the endoplasmic reticulum (FIG. 22B), indicating that prognosis after glioma surgery can be predicted by examining GFRα4 relocation.

Example 17

Figure 23:
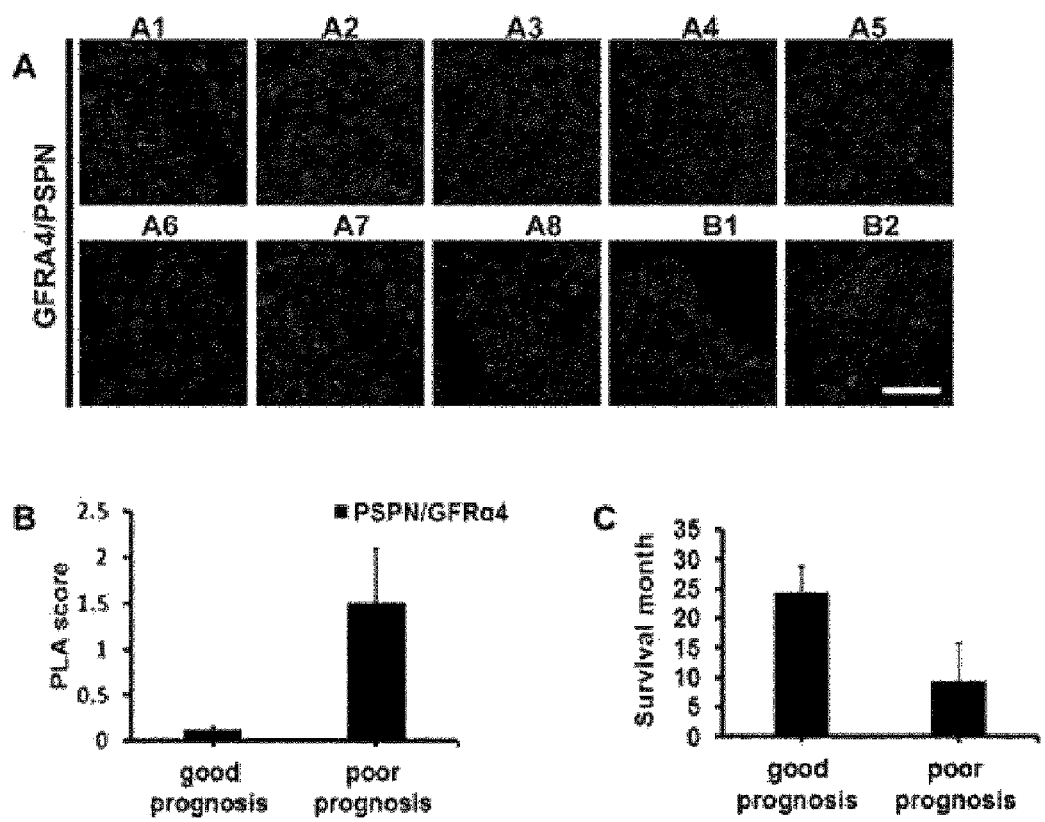
FIG. 23 shows that prognosis after glioma surgery is poorer, as the number of GFRα4 and PSPN interactions is increased.

Effect of Changes in the Number of Interactions between PSPN and GFRα4 in Patient After Glioma Surgery on Prediction of Prognosis After Glioma Surgery In the present invention, a correlation between changes in the number of interactions between PSPN and GFRα4 in patients after glioma surgery and prediction of prognosis after glioma surgery was examined. As a result, as prognosis after glioma surgery was poorer, the number of interactions between PSPN and GFRα4 was increased (FIGS. 23A & B).

It was also confirmed that prediction of prognosis after glioma surgery by examining the number of interactions between PSPN and GFRα4 is associated with survival rate after surgery (FIG. 23C), suggesting that it is possible to predict prognosis after glioma surgery by examining the number of interactions between PSPN and GFRα4.

It will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

EFFECT OF THE INVENTION

Subcellular locations of one or more proteins selected from the group consisting of GFRα4, PSPN, KIF13A, RNF138, TLX3, ATIC, DIP2A, STAT3, DLX2, TBX19, AGAP1, CPB1, NFRκB, ARHGEF15, CLK2 and SYT9 of the present invention are changed in glioma cells. Therefore, by comparing their expression levels in the particular subcellular locations, accurate diagnosis of glioma can be made, progression of glioma can be diagnosed, and prognosis after glioma surgery can be predicted. In addition to subcellular locations of proteins, the number of protein-protein interactions is also measured to demonstrate the function and mechanism of proteins involved in glioma progression.

What is claimed is:

1. A method for screening a therapeutic agent for glioma, comprising:
   treating nerve cells with a candidate therapeutic agent for glioma;
   comparing the GFRα4 relocation from the endoplasmic reticulum to the plasma membrane in said treated nerve cells with GFRα4 relocation from the endoplasmic reticulum to the plasma membrane in a control group that is treated with no candidate therapeutic agent; and
   identifying a candidate therapeutic agent when said candidate therapeutic agent causes a relocation of GFRα4 from the endoplasmic reticulum to the plasma membrane in said treated nerve cells as compared to said control group.

2. A method for screening a therapeutic agent for glioma, comprising:
   treating nerve cells with a candidate therapeutic agent for glioma; and
   comparing its inhibition of GFRα4 expression in the endoplasmic reticulum with that of the control group that is treated with no candidate therapeutic agent.

* * * * *